(12) United States Patent  
Atzler et al.

(10) Patent No.: US 9,188,527 B2  
(45) Date of Patent: Nov. 17, 2015

(54) MONOCHROMATOR-BASED AND FILTER-BASED DETECTION SYSTEM

(71) Applicant: Molecular Devices, LLC, Sunnyvale, CA (US)

(72) Inventors: Josef J. Atzler, Hallein (AT); Georg Kronberger, Salzburg (AT); Steven Boege, San Mateo, CA (US)

(73) Assignee: Molecular Devices, LLC, Sunnyvale, CA (US)

( * ) Notice: Subject to any disclaimer, the term of this patent is extended or adjusted under 35 U.S.C. 154(b) by 278 days.

(21) Appl. No.: 13/737,304

(22) Filed: Jan. 9, 2013

(65) Prior Publication Data

US 2014/0191138 A1    Jul. 10, 2014

(51) Int. Cl.
*G01N 21/31*  (2006.01)
*G01N 21/64*  (2006.01)

(52) U.S. Cl.
CPC .............. *G01N 21/31* (2013.01); *G01N 21/645* (2013.01)

(58) Field of Classification Search
CPC .............................. G01N 21/64; G01N 21/645
See application file for complete search history.

(56) References Cited

U.S. PATENT DOCUMENTS

| 6,580,081 | B1 * | 6/2003 | Thorwirth | 250/458.1 |
| 8,968,658 | B2 * | 3/2015 | Katzlinger et al. | 422/67 |
| 2005/0023445 | A1 * | 2/2005 | Horn et al. | 250/214 R |

* cited by examiner

*Primary Examiner* — David Porta
*Assistant Examiner* — Faye Boosalis
(74) *Attorney, Agent, or Firm* — Bella Fishman

(57) ABSTRACT

A system is provided for performing filter-based and monochromator-based measurements. The system includes a light source and a plurality of detectors. An excitation monochromator outputs a selected wavelength component of the excitation light. Emitted light from a sample follows a selected emission optical path. An emission monochromator outputs a selected wavelength component of the emitted light when part of the selected path. An interface cartridge includes emission light ports positioned to direct the emitted light from the sample along a corresponding optical path. The interface cartridge aligns a selected optical path with the main measurement optical axis. A movable sliding switch mechanism provides optical channels corresponding to positions on the sliding switch mechanism to complete a selected emission optical path. The position on the sliding switch mechanism is selected by moving the sliding switch mechanism to align the optical channel for the position with the main measurement optical axis.

21 Claims, 24 Drawing Sheets

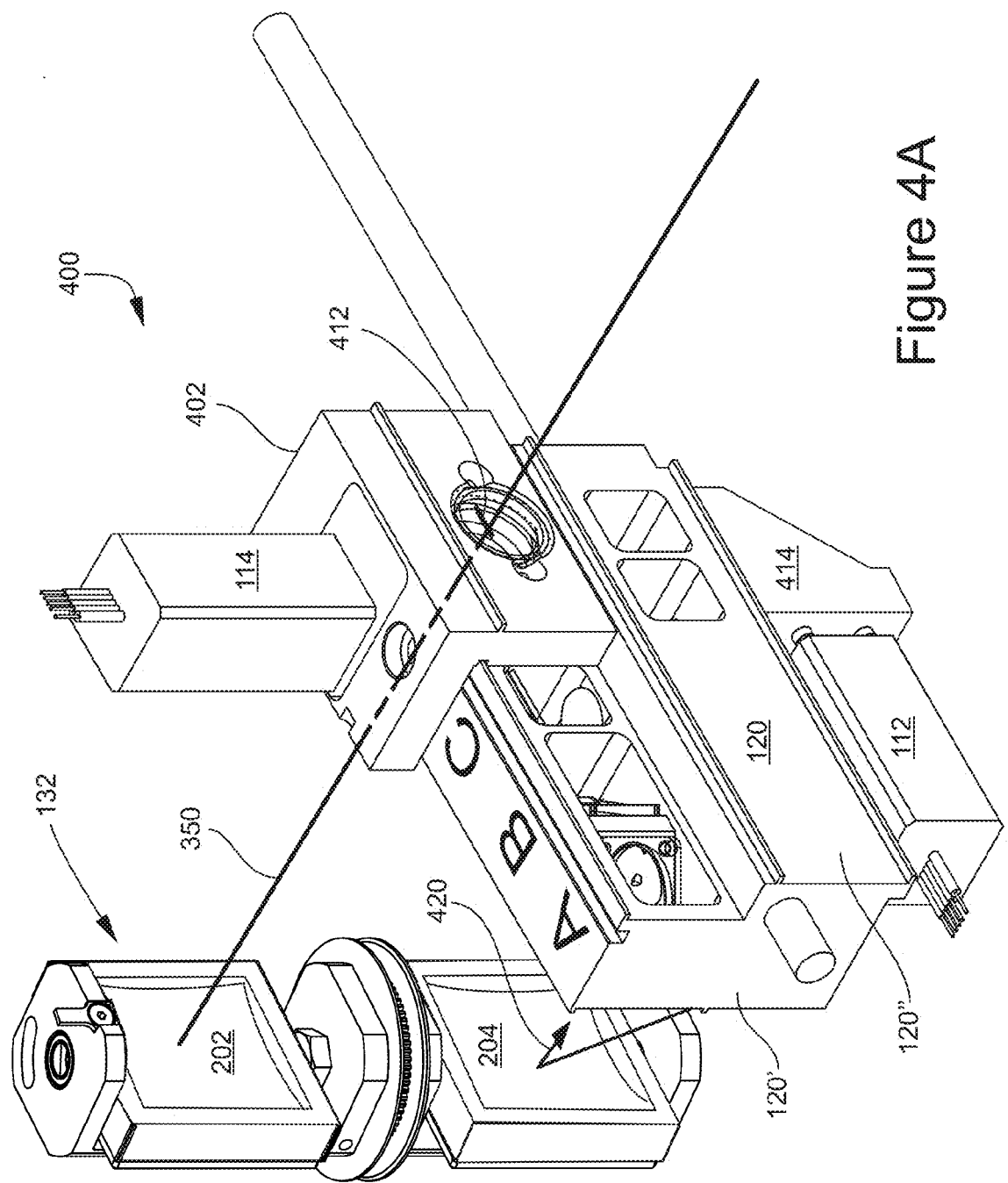

MONOCHROMATOR-BASED AND FILTER-BASED DETECTION SYSTEM

RELATED APPLICATIONS

U.S. patent application Ser. No. 13/166,595, filed on Jun. 22, 2011, and titled "OPTICAL DETECTION UTILIZING CARTRIDGE WITH TUNABLE FILTER ASSEMBLY," is incorporated by reference herein in its entirety.

TECHNICAL FIELD

This present invention generally relates to analytical instruments and methods related to such instruments, and more particularly, to fully functionally expandable monochromator-based and filter-based systems.

BACKGROUND

Multimode analytical instruments, also referred to as multimode readers, are apparatus that can perform multiple analytical assays in a single instrument. Standard multimode readers, used within the life science industry, can measure the most common types of assays (i.e., applications, such as fluorescence, luminescence, and absorbance) in a single instrument. The use of a single instrument to perform these assays is advantageous over using multiple dedicated instruments to perform the same measurements. This lies in the fact that a multimode reader can provide ease of use, a better price performance ratio, and require less bench top area than multiple instruments.

Generally, these instruments have built-in general purpose (i.e., white) light sources, such as halogen lamps and xenon flash lamps, and general purpose detectors such as photomultiplier tubes (PMTS) and silicon photodiodes. The instruments also typically include optical filters mounted into wheels or slides, and application specific beamsplitters installed into slides, or into revolver like mechanisms. Multimode readers may also combine filter-based and monochromator-based technology. While components are configured to perform a variety of types of assays, expanding the multimode reader to perform new assays and new applications was often difficult. From a hardware point of view, specific applications may involve accessing a multitude of driven stages for selecting the correct combination and adjustment of filters, beamsplitters, apertures, and light-guides, for example. In these devices, enabling new applications of a given technology required retrofitting specific optical filters and beamsplitters. Adding new applications often required substantial redesign.

The implementation of standardized application cartridges having a standard form and shape, and configured with components arranged for specific applications, or types of applications has improved the ability add applications. One example of a system that employs application cartridges is the Paradigm® system from Molecular Devices. Application cartridges substantially reduce the amount of redesign and retrofitting involved in adding applications to a system. However, with the exception of applications that employ absorbance-based measurements, the advantages have largely been realized for filter-based technologies. Applications that involve fluorescence-based and luminescence-based measurements and that also use monochromator-based technology have not been successfully implemented in standard cartridges. In general, the standard cartridges lack the size to accommodate such applications. It would be desirable for a multimode reader to be truly expandable so that applications can be added to the system without any significant redesign.

Detection systems that use multimode readers typically take measurements from samples in microplates. Cell imaging systems have recently included functions that incorporate components typically found in detection systems. For example, detectors may be incorporated for performing label-free detection to measure changes in refraction index of microplate bottoms after reagent addition. Detection systems incorporate illumination and injection functions that may be advantageously used by cell imaging systems. For example, the illumination components in detection systems such as photodiodes may be used in a cell imaging system to perform epifluorescent microscopy.

There is a need in the art for a detection system with multimode reader capabilities that would not require any redesign in incorporating new technologies and new applications, including those that involve monochromator-based technology in fluorescent and luminescent measurements. There is also a need in the art for a detection system that would permit an interface with a cell imaging system in order to enable the advantageous use of components in the detection system in the cell imaging system.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a system is provided for analyzing a target in a sample capable of generating an emitted light. The system includes an excitation light source configured to generate an excitation light along an excitation optical path. The system includes a plurality of detectors configured to measure an optical characteristic in an emission light. The plurality of detectors includes at least one monochromator-based measurement detector. An excitation monochromator is configured to receive the excitation light and to output a selected wavelength component of the excitation light along the excitation optical path when the target in the sample generates the emitted light in response to the excitation light. A sample carrier positions the sample to receive the excitation light and to generate the emitted light along one of a plurality of selectable emission optical paths. A cartridge carrier supports a plurality of removable cartridges having a common form factor. The cartridges may include application cartridges that support filter-based measurements. The cartridge carrier is configured to move the removable cartridges to a selected position. An emission monochromator is configured to receive the emitted light from the sample along a main measurement optical axis, and to output a selected wavelength component of the emitted light along the selected emission optical path when the selected one of the plurality of selectable emission optical paths includes the emission monochromator. An interface cartridge is provided with the common form factor for removably mounting on the cartridge carrier. The interface cartridge includes a plurality of emission light ports each positioned to direct the emitted light from the sample along a corresponding one of a plurality of optical paths. The interface cartridge is positioned to align a selected one of the plurality of optical paths with the main measurement optical axis. The system includes a movable sliding switch mechanism comprising a plurality of optical channels each corresponding to a position on the sliding switch mechanism. Each optical channel is configured to complete a corresponding one of the plurality of selectable emission optical paths. The position on the sliding switch mechanism is selected by moving the sliding switch mechanism to align the optical channel for the position with the main measurement optical axis.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 4A is a perspective view of an example implementation of a sliding switch mechanism.

DETAILED DESCRIPTION

I. Monochromator-Based and Filter-Based Detection System-Overview

Figure 1A:
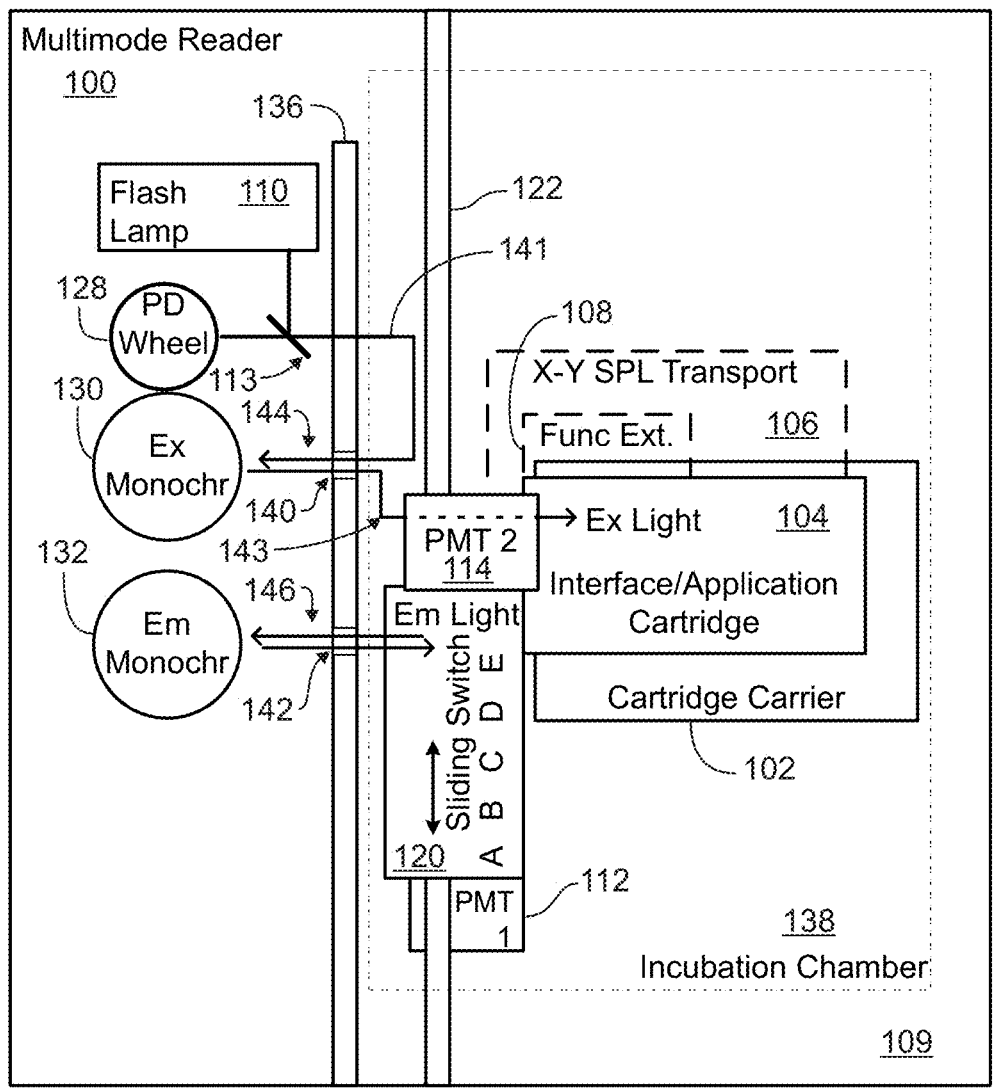
FIG. 1A is a schematic top view of an example of a monochromator-based and filter-based detection system.

Examples of a detection system that supports new applications employing monochromator-based and filter-based technologies are described below. The detection system includes a cartridge carrier and other resources for using standard cartridges that may already exist. The detection system also includes monochromators, an optical configuration panel, adjustable connection optics modules, a flash module, a multiple high-power light-emitting diode ("LED") assembly, at least one photomultiplier tube ("PMT"), and a sample support. The monochromators, flash module, PMT, LED assembly, optical configuration panel, and sample support are affixed to the base unit of the detection system.

The monochromators may include an excitation monochromator to set an excitation light for illuminating a sample to a selected wavelength, and an emission monochromator to set an emission light generated by the illuminated sample to a selected wavelength. The optical configuration panel may provide selectable filters such as, for example, polarizing filters, attenuating filters, order sorting filters, and any other desired filter, in either an excitation optical path or an emission optical path. The adjustable connection optics modules may include an interface cartridge that may be used as an application cartridge by removably inserting into the cartridge carrier. The adjustable connection optics modules may also include a sliding switch mechanism comprising multiple optics ports for directing optical paths in accordance with specific applications. The sliding switch mechanism is configured to slide into selected positions in response to a motorized linkage that is controlled by a system controller. The interface cartridge and sliding switch mechanism may be controlled to provide alternative optical paths between a light source and a detector according to the specifications of an application. The alternative optical paths may be selected to pass through excitation and/or emission monochromators, to select a light source for the excitation optical path, and to select a detection device for obtaining a measurement.

The light source and detector is selected according to the application. In some applications, the light source is the flash lamp, which generates an excitation light along an excitation light path formed by fixed connection optics in the detection system and either the interface cartridge or an application cartridge; either cartridge being configured with optics directing the excitation light towards the sample in the sample support. In some applications, the light source may be a high-power LED that generates light within a selected bandwidth. In other applications, the light source may also be in an application cartridge, which may be configured to direct the excitation light directly to the sample, and emitted light from the sample to be measured may be directed to a selected one of the detectors. In applications that operate using the interface cartridge, the excitation light may be directed to the sample via the excitation monochromator, or via a path that bypasses the excitation monochromator.

The applications may select a detector from either a photodiode, a standard PMT, or a specialized PMT. The specialized PMT may be deemed an option for configuration by specific customers in example implementations.

It is noted that example implementations described below incorporate solutions that enable the use of existing application cartridges that may be made for use with a cartridge-based multimode reader system, such as for example, the Paradigm® system. Example implementations described below make advantageous use of the common form factor of the existing application cartridges. The common form factor relative to the existing application cartridges relied upon in the example implementations described below incorporate dual optical emission paths via an upper and a lower optical access port in the cartridge. The upper, the lower or both optical emission paths may be aligned with optical paths that extend to an application-appropriate detector. The emission paths are directed from a sample that generated the emitted light. The sample may be located on a multiple sample plate, such as a microplate mounted on an x-y movable sample carrier positioned in the bottom of the system, or underneath the cartridge carrier and any optical components needed to guide optical paths to and from the samples.

In the description that follows, reference is made to the terms "top," "bottom," "upper" and "lower" to describe the relative position of various optical paths and components. The following definitions provide a reference for how terms "top," "bottom," "upper" and "lower" are to be understood in the description below:

Upper cartridge paths: Optical paths aligned with the "upper" port of the cartridge. The "upper cartridge path" term applies to either an existing application cartridge, or the interface cartridge (described below).

Lower cartridge paths: Optical paths aligned with the "lower" port of the cartridge. The "lower cartridge path" term applies to either an existing application cartridge, or the interface cartridge (described below), however, with respect to the interface cartridge, the lower cartridge paths refer primarily to excitation paths.

Upper monochromator paths: Optical paths aligned with the upper grating of either the excitation monochromator or the emission monochromator that implement a double grating monochromator.

Lower monochromator paths: Optical paths aligned with the lower grating of either the excitation monochromator or the emission monochromator.

Top fluorescent measurement paths: Excitation or emission paths involving a fluorescent measurement from above the sample using fluorescent optical paths provided by the interface cartridge and the sliding switch mechanism as described below, or by existing application cartridges.

Bottom fluorescent measurement paths: Excitation or emission paths involving a fluorescent measurement from under the sample using a bottom fluorescence optics module described in further detail below.

Top: In general, the term "top" refers to the portion of the system that is above a bottom plate supporting the interface cartridge and any optical components above the sample.

Bottom: In general, the term "bottom refers to the portion of the system that is underneath the bottom plate and the samples.

It is to be understood that while the common form factor followed by existing application cartridges may be the basis for the layout of the components in the example implementations described below, the common form factor is not intended to limit the invention to any particular layout of components. Other existing application cartridges that are different from the application cartridges referenced here may provide an alternative common form factor. In addition, example implementations may not rely on any common form factor based on any pre-existing application cartridge or system. It is to be understood that any reference to "existing application cartridge" may also refer to a future application cartridge configured to operate while mounted in the cartridge carrier of the detection system.

Figure 1B:
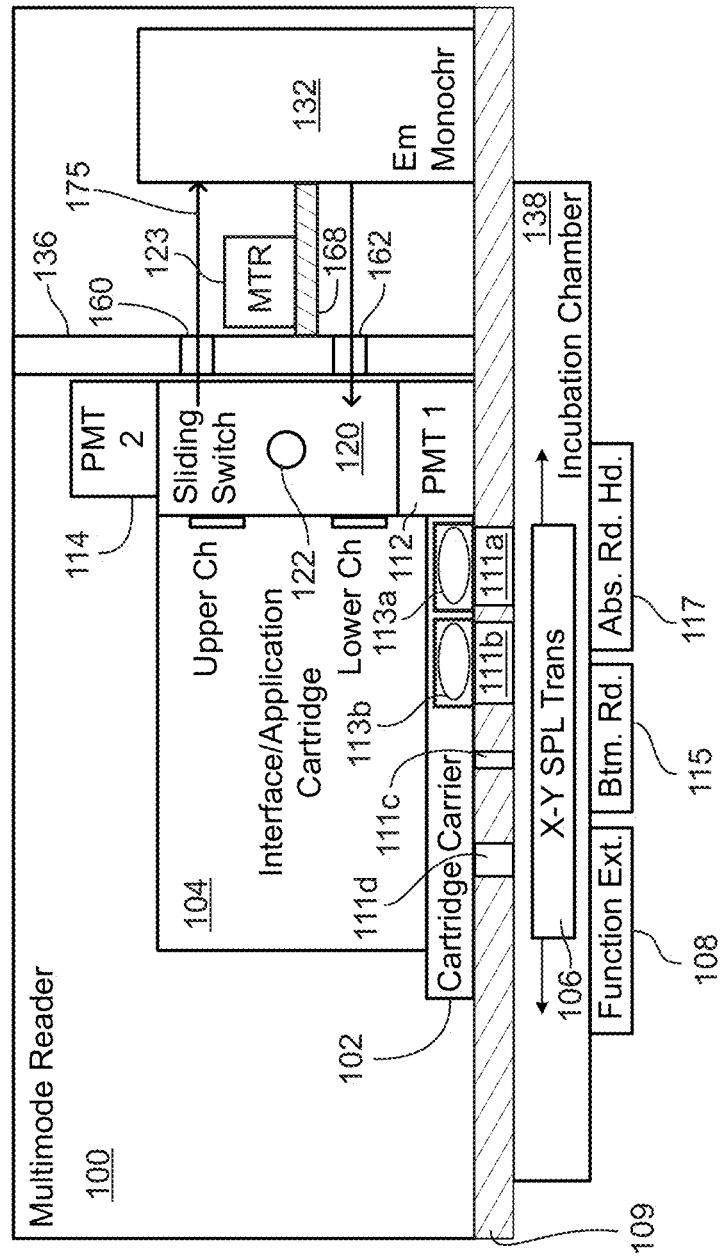
FIG. 1B is a schematic side view of the monochromator-based and filter-based detection system in FIG. 1A.

FIG. 1A is a schematic top view of an example of a monochromator-based and filter-based detection system 100. FIG. 1B is a schematic side view of the monochromator-based and filter-based detection system 100 in FIG. 1A. It is noted that the term "multimode reader" is used interchangeably with "detection system" in this description. The detection system 100 in FIG. 1A includes a cartridge carrier 102 configured to support one or more application cartridges 104. The cartridge carrier 102 and application cartridges 104 may be designed to provide support for existing applications and technologies, such as for example, applications and cartridges provided by the Paradigm® detection system. The application cartridges 104 may also be future cartridges configured to operate with a common form factor dictated by an interface cartridge that may operate as an application cartridge as described below.

The detection system 100 also includes a sample support 106, which is shown in FIGS. 1A and 1B as being positioned underneath a bottom plate 109 of the detection system 100 and inside an incubation chamber 138. The sample support 106 may be implemented as a carrier for multiple samples removably mounted on an x-y transport. The samples may be placed in sample holders or wells arranged on a planar tray structure. In the example implementations described herein, the multiple sample holder is implemented using a microplate, which is known in the art as a sample holder typically used in detection systems. The reference herein to a microplate is not however intended as limiting. Those of ordinary skill in the art would understand that other suitable sample holders may be used as well. It is to be understood that the sample support 106 refers to the microplate and x-y transport as a unit in this description.

The detection system 100 includes a light source implemented using a flash lamp module 110, and an LED wheel 128. As described in more detail below with reference to FIG. 2C, the flash lamp module 110 or an LED on the LED wheel 128 generates an excitation light along an excitation light path 141, which is directed through the system using directing optics devices strategically placed in the system housing. Directing and selecting optics, such as an excitation light splitter 113, may be controlled to guide a selected excitation light from either the flash lamp module 110 or the LED wheel 128. The flash lamp module 110 may be any suitable flash lamp, such as a Xenon flash lamp, and an interface for controlling on/off state, duty cycle, and any other parameters that may be advantageously controlled for the applications performed by the system 100. The LED wheel 128 includes a plurality of high-powered LEDs positioned on the periphery of the LED wheel 128, which may be rotated using a motor to insert the selected LED in the excitation light path 141.

The detection devices are implemented in the detection system 100 using an absorbance detector (such as a photodiode, for example) mounted on an absorbance reader module 117 in FIG. 1B, a first PMT 112, and a second PMT 114. The absorbance read head 117, a bottom fluorescence optics module 115, and a function expander module 108 may be mounted under the bottom plate 109 of the housing. In addition, as shown in FIG. 1B, the absorbance reader module 117, the bottom fluorescence optics module 115, and the function expander module 108 are mounted under the incubation chamber 138, which holds the sample support 106.

The bottom plate 109 may include four openings. A first opening 111a provides access for an excitation light along an excitation optical path aligned with an absorbance lens assembly 113a and a sample on the sample carrier to perform absorbance measurements. A second opening 111b in the bottom plate 109 provides access for optical paths formed for top-side fluorescence and luminescence measurements and aligned with a top fluorescence/luminescence lens assembly 113b. A third opening 111c in the bottom plate 109 may be used to insert a light guide into the incubation chamber 138 in close proximity to a selected sample in the sample carrier that may be used to receive luminescence emission light in accordance with specific applications. A fourth opening 111d in the bottom plate 109 may be used for access by components in the function expander module 108. In an example implementation, the function expander module 108 may be an imaging system interface that permits a cell imaging system under the multimode reader 100 to use resources available on a cartridge, such as illuminating functions or fluid injection functions as described below.

The first PMT 112 may be a standard photomultiplier tube that may be used in most applications performed by the system 100. The second PMT 114 may be a specialized photomultiplier tube such as for example a UV/VIS (for measuring ultraviolet as well as visible light) or a UV/VIS/NIR (for measuring ultraviolet or near infrared as well as visible light). The second PMT 114 may be designated as optional in example implementations such that it is installed per customer specification.

The system 100 includes an excitation monochromator 130 and an emission monochromator 132 configured to receive a light and to transmit the light at a selected wavelength. The system also includes an optical configuration panel 136 that may be used to configure the direction and characteristics of the optical paths between light source and detectors, and to control light transmission into and out of the excitation monochromator 130 and emission monochromator 132. The optical configuration panel 136 may include a first set of optical ports 140 for directing the excitation light path 141 to and from the excitation monochromator 130 and a second set of optical ports 142 for directing an emission light path to and from the emission monochromator 132.

The excitation monochromator 130 may be controlled to spread the received excitation light into its component wavelengths and to output a selected one of the wavelengths along the excitation light path 141. Particular applications may operate with an excitation light at a particular wavelength. The excitation monochromator 130 may receive the generally white light generated by the flash lamp module 110 and outputs the excitation light at the wavelength selected for the application.

The excitation monochromator 130 and the emission monochromator 132 may be implemented as double stacked gratings configured as a subtracting double monochromator. The excitation monochromator 130 and the emission monochromator 132 may be enclosed in a substantially wall-off chamber that may include a middle plate 168 between the top and bottom gratings of each monochromator.

Particular applications may also require measurement of an emitted light from a sample at a selected wavelength. The emitted light from the sample may be directed to the second set of optical ports 142. An input emission light 146 is directed from the second set of ports 142 to the emission monochromator 132. The emission monochromator 132 directs the selected wavelength component of the emission light 142 to the second set of ports 142 towards optics that directs the emission light towards a selected detector.

In the example implementation described here with reference to FIGS. 1A, 1B, and 2, the excitation monochromator 130 and emission monochromator 132 may be implemented as top and bottom level monochromators. For example, in FIG. 1B, the emission monochromator 132 includes a top level that receive the emission light 146 at an emission monochromator entrance slit 160 on the optical configuration panel 136. The top level of the emission monochromator 132 includes a top grating, which spreads the emission light on the emission light path 146 into multiple light paths each at the component wavelengths of the emission light. A mirror on the optical configuration panel 136 is positioned at an angle for receiving the selected wavelength component of the emission light. The selected wavelength component of the emission light is directed to another mirror on the optics configuration pane, which directs the emission light to the lower level grating of the emission monochromator 132. The emission light is again spread into its component wavelengths, which may be limited substantially to the wavelength selected for the top level of the emission monochromator 132. The lower level of the emission monochromator 132 is positioned to place the selected wavelength component of the emission light at an emission monochromator exit slit 162.

The emission monochromator entrance slit 160 and emission monochromator exit slit 162 accommodate the two-level grating structure of the emission monochromator 132. The dual-level optical path options available using the emission monochromator entrance slit 160 and emission monochromator exit slit 162 may also accommodate a dual-channel optical path format of the cartridges used as application and/or interface cartridges 104.

Application cartridges may be used to perform measurements according to existing applications available prior to an implementation of the system 100, or after to conform to the system 100. An interface cartridge may be used to perform measurements using a variety of detection modes. Emphasis in the description of example implementations below is placed on the interface cartridge. Accordingly, the term "interface cartridge 104" is used in place of the term "application and/or interface cartridge 104" except where the context warrants the use of the term "application and/or interface cartridge 104."

The interface cartridge 104 includes optical components arranged to provide multiple paths for excitation and emission light paths that are selectable according to specific applications, or more specifically, specific detection modes. For example, the interface cartridge 104 may be moved to a position that guides the excitation light path 144 exiting the excitation monochromator 130 to the sample on the sample support 106 for an absorbance measurement. The interface cartridge 104 may also include an optics path that guides the excitation light path 144 through fluorescence measurement optics, which directs the excitation light to the sample and the emission light generated by the sample to one of the detectors.

The interface cartridge 104 may be used in conjunction with a sliding switch mechanism 120 to configure optics paths between light source and detectors for applications that involve using monochromators, the flash lamp module 110, the LED wheel 128 and any of the detectors (photodiode and PMTs). The interface cartridge 104 and the sliding switch mechanism 120 are movable to enable positioning the interface cartridge 104 and the sliding switch mechanism 120 in position to provide a desired light path. The interface cartridge 104 may be moved by positioning the cartridge carrier 102, and the sliding switch mechanism 120 may be moved by a motor in conjunction with a sliding switch guide rail 122.

II. Hybrid Multimode Reader

Example implementations of the various components of the system 100 described above with reference to FIGS. 1A & 1B are described in more detail below with particular reference to FIGS. 2-7.

A. Light Source Assembly

The system 100 includes a light source assembly capable of generating an excitation light from LEDs and from a flash lamp. The excitation light generated by either the flash lamp or an LED may be processed using an excitation monochromator to select a wavelength, or a range of wavelengths to include in the excitation light. An example monochromator that may be used for the excitation monochromator is described with reference to FIG. 2A. An example LED wheel for selecting one of a plurality of LEDs to generate the excitation light is described with reference to FIG. 2B. An example configuration for a flash lamp module and optical path for selecting between the LED and flash lamp light sources is described with reference to FIG. 2C. An excitation light path for an absorbance measurement is described with reference to FIG. 2D.

1. Monochromators

Figure 2A:
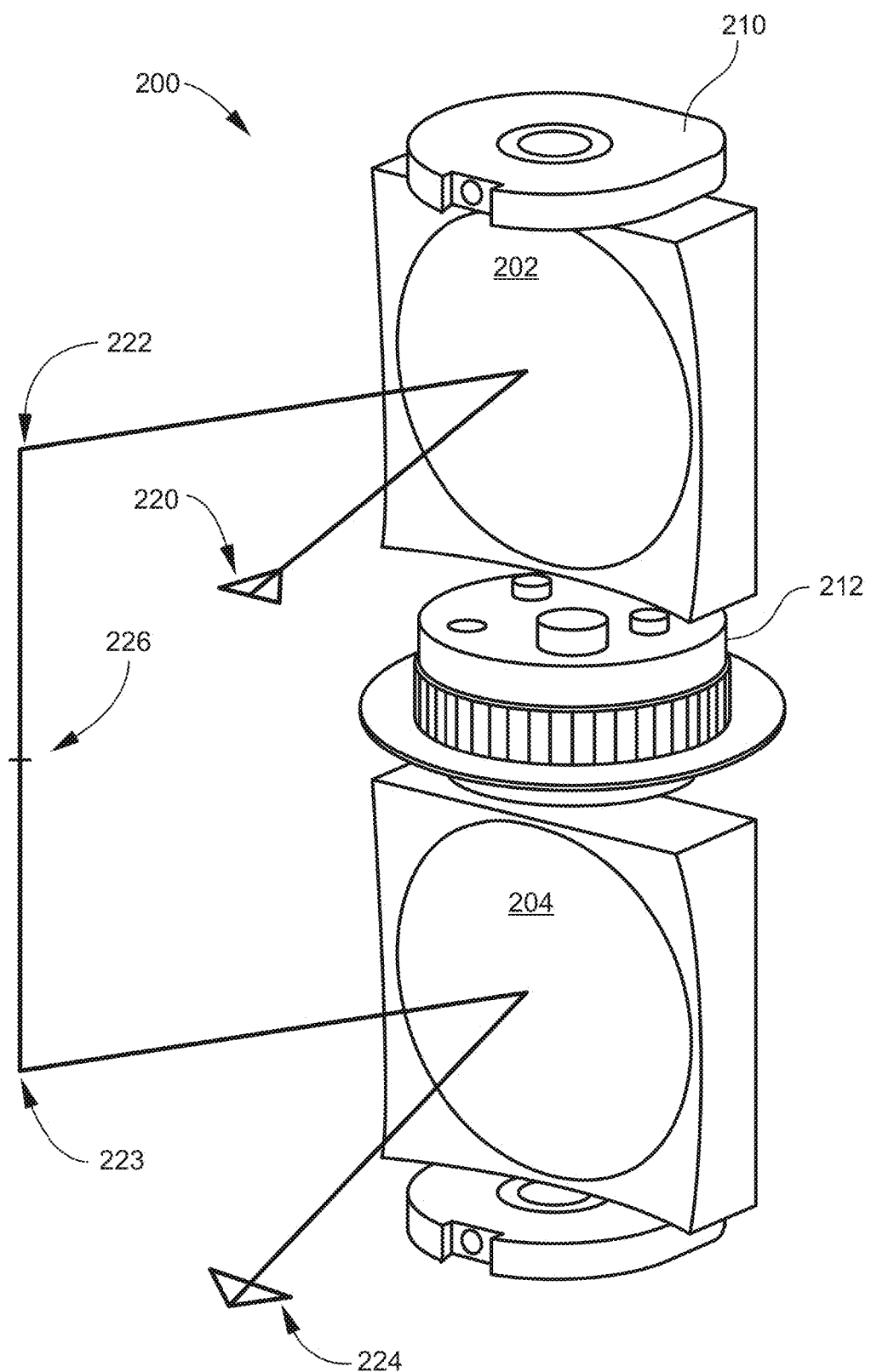
FIG. 2A is a perspective view of an example of a pair of gratings arranged as a top and a bottom grating that may be used in an excitation or emission monochromator in the example illustrated in FIGS. 1A and 1B.

FIG. 2A is a perspective view of an example of a monochromator 200 that may be used as an excitation monochromator in the example illustrated in FIGS. 1A and 1B. As noted below, the monochromator 200 described with reference to FIG. 2A may also be used for the emission monochromator in FIGS. 1A and 1B. The monochromator 200 in FIG. 2A includes a first grating 202 and a second grating 204 stacked on top of the first grating 202. A top monochromator bearing 210 is positioned on top of the first grating 202 and a gearwheel 212 is positioned between the first grating 202 and the second grating 204. The top monochromator bearing 210 and the gearwheel 212 are controlled to rotate the gratings to perform the wavelength selection function of the monochromator 200. The gearwheel 212 may be controlled by a belt that is turned by a motor located near the gearwheel 212.

The first grating 202 and the second grating 204 are arranged to operate as a subtracting double monochromator. The first grating 202 receives an unprocessed light from an entrance slit (indicated, but not shown, at 220) and spreads the unprocessed light into its spectral components. The first grating 202 is rotated so that a selected color (or wavelength or spectral portion of a range of wavelengths) is directed towards a first guiding mirror 222. The first guiding mirror 222 reflects the light at the selected wavelength to another guiding mirror 223, which directs the light at the selected wavelength towards the second grating 204. The second grating 204, which turns in tandem with the first grating 202, operates in reverse by combining the range of wavelengths received from the first grating 202 into homogeneous light. The dispersion subtracting effect eliminates stray light from the homogeneous light that is then directed towards an exit slit (indicated at 224). A middle slit 226 may be provided as an exit slit for an upper monochromator (first grating), and an entrance slit for the lower monochromator (second grating). It is noted that the entrance slit at 220, the first and second guiding mirrors 222, 223, the exit slit at 224 and middle slit 226 may be mounted on a structure that may provide an enclosure for the monochromator 200. In an example implementation described in more detail below, these components are mounted on the optics configuration panel 136 (in FIGS. 1A & 1B).

2. LED Wheel

Figure 2B:
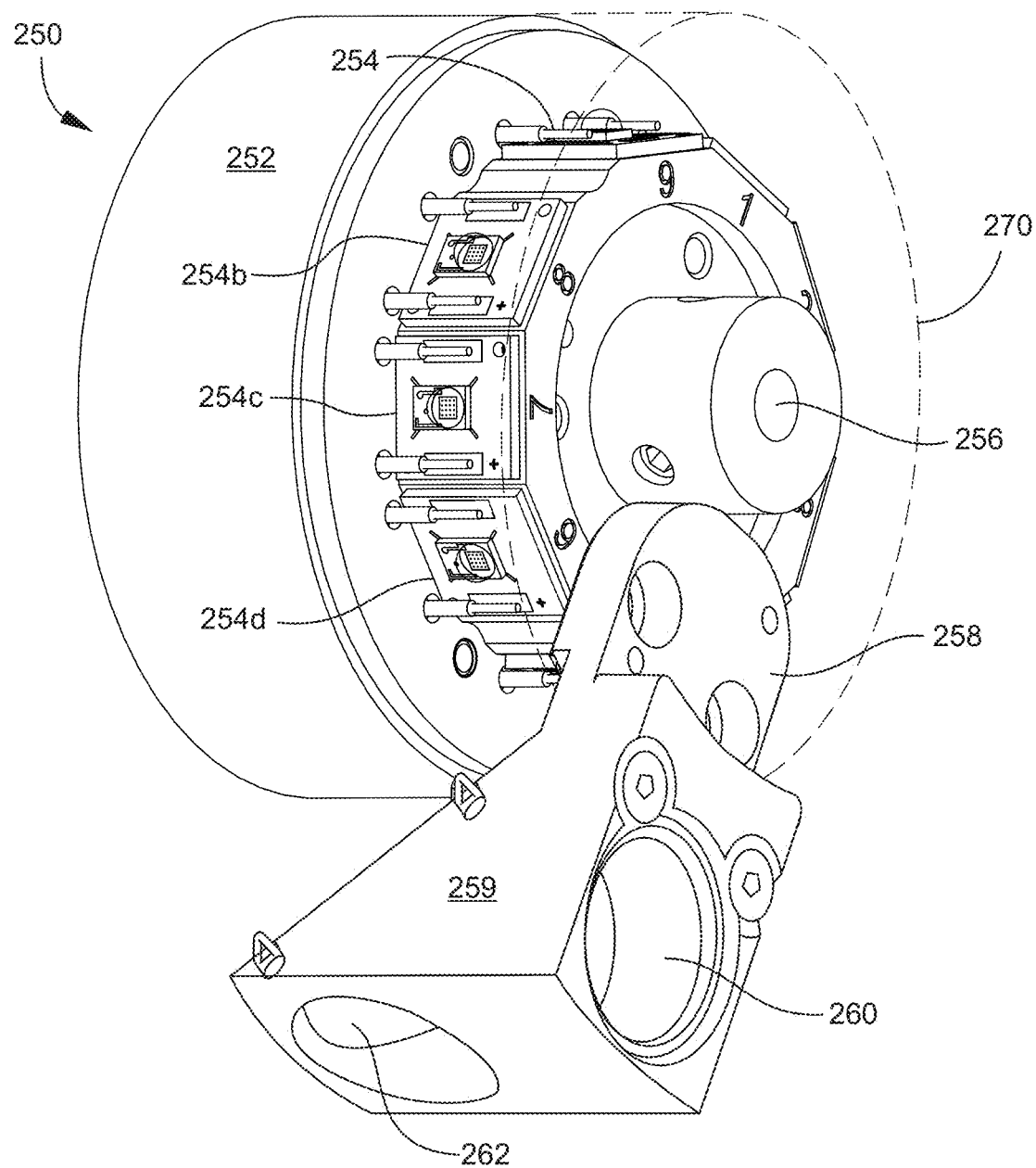
FIG. 2B is a perspective view of an example of an LED wheel that may be used in the example system in FIGS. 1A and 1B.

FIG. 2B is a perspective view of an example of an LED wheel 250 that may be used in the example system in FIGS. 1A and 1B. The LED wheel 250 in FIG. 2B includes a wheel housing 252 configured to support a plurality of LED modules 254. FIG. 2B shows the LED wheel 250 includes a first LED module 254a, a second LED module 254b, a second LED module 254c, and a fourth LED module 254d. The LED modules 254 each comprise a high-power LED that generates light at a given wavelength. In an example implementation of the LED wheel 250, a desired wavelength range may be about −450 nm to −700 nm, and nine LED modules are provided in the LED wheel 250 selected to generate light that spans the desired wavelength range.

The LED wheel 250 includes a motor shaft opening 256 configured to fit a wheel motor axis and to suitably engage the wheel motor axis allowing the LED wheel 250 to turn as controlled by a wheel motor (described below with reference to FIG. 2C). The LED wheel 250 also includes a wheel bracket 258 and an exit optics housing 259. The wheel bracket 258 permits mounting of the LED wheel 250 in an assembly that provides a link with the flash lamp module (described below with reference to FIG. 2C). The exit optics housing 259 includes an optional interference filter 260 and an excitation light beam splitter 262. The excitation light beam splitter 262 directs either a light from one of the LEDs in the LED wheel 250 or a light from the flash lamp module along an excitation light path. The exit optics housing 259 may also include an LED objective lens (not shown in FIG. 2B) for the light generated by the selected LED module 254 on the LED wheel 250.

The LED wheel 250 in FIG. 2B includes a cover 270 to minimize stray light, either coming in from outside the LED wheel 250 or leaching out from the LED wheel 250. The cover 270 may include port holes 273 aligned with each LED on the LED modules 254 to enable the light to exit from the LED modules 254 along the excitation light path.

In operation, the LED wheel 250 is rotated by a controller configured to position the LED wheel 250 that aligns an LED module 254 having an LED with a desired wavelength with an optical path directed towards the excitation light beam splitter 262.

3. Flash Lamp Module and Optional Excitation Paths

Figure 2C:
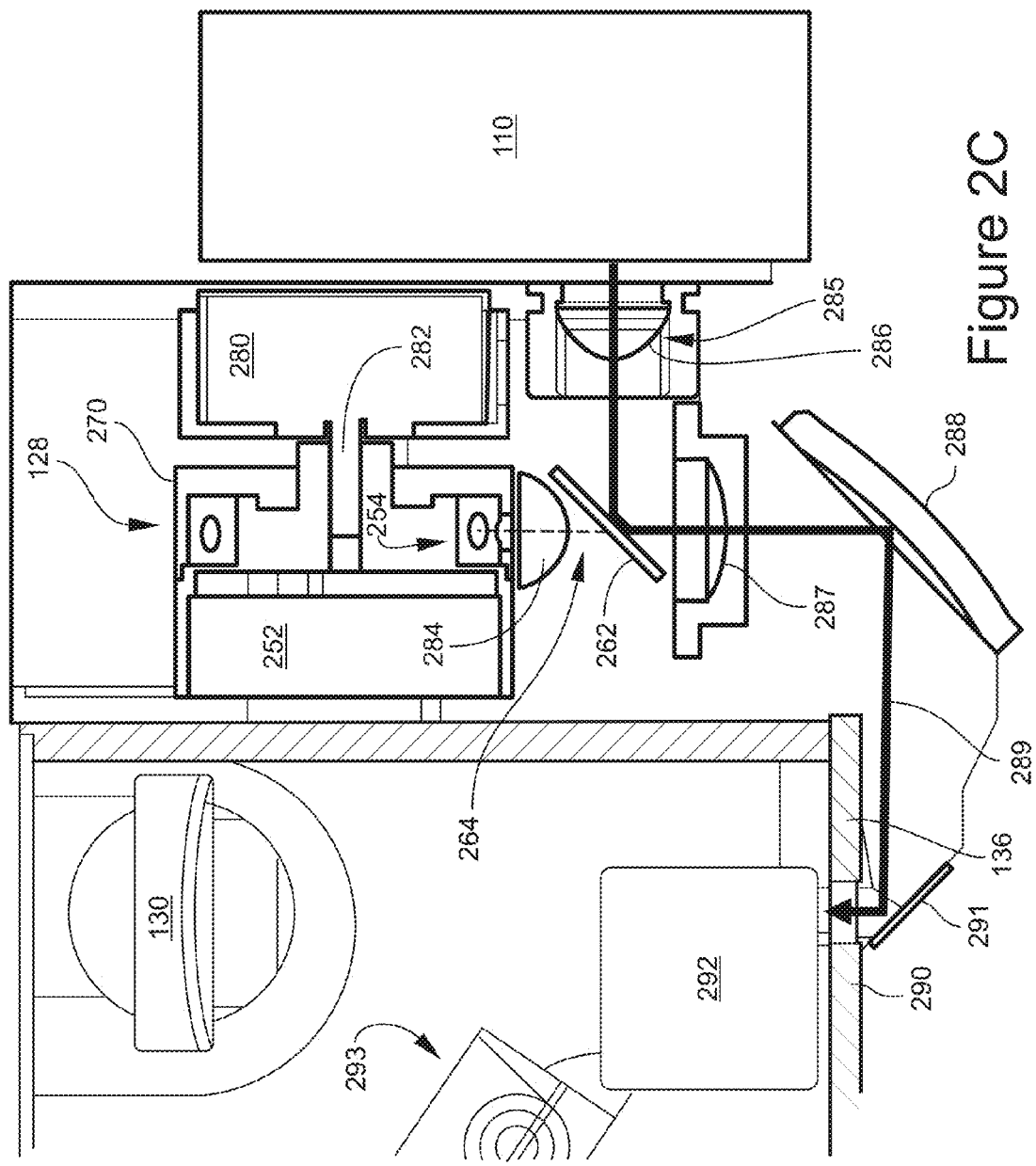
FIG. 2C is a top view of an example implementation of an excitation light assembly that may be used in the system shown in FIGS. 1A and 1B.

FIG. 2C is a top view of an example implementation of an excitation light assembly that may be used in the system shown in FIGS. 1A and 1B illustrating the flash lamp module 110, the LED wheel 128, and optional excitation light paths. The LED wheel 128 is depicted as being vertically mounted with an LED wheel motor 280 mounted between the LED wheel 128 and the flash lamp module 110. The LED wheel motor 280 includes a wheel motor shaft 282 inserted in the wheel motor shaft opening 256. An LED module 254 on the LED wheel 128 is selected for generating light by turning the LED wheel 128 until the selected LED module 254 is aligned with an excitation light path 289. The light from the selected LED module 254 is directed out through an LED wheel objective 284 and along an LED light path 264 towards the excitation light beam splitter 262. The excitation light beam splitter 262 directs the LED light along the excitation light path 289 towards the excitation monochromator 130.

The flash lamp module 110 is mounted in the assembly such that the flash lamp generates light in a direction that is perpendicular to that of the LED wheel 128. The flash lamp light exits the flash lamp module 110 at a flash lamp optical housing 285, which contains a flash light objective lens 286. The flash lamp light follows a path to the excitation light beam splitter 262, which reflects the flash lamp light on to the excitation light path 289. From the excitation light beam splitter 262, the excitation light path 289 is the same for both the flash lamp light and the LED light. The excitation light path 289 is directed through a common excitation light lens 287 and reflects off a first excitation path mirror 288, which may be 90° off-axis elliptical mirror. The first excitation path mirror 288 directs the excitation light path 289 towards an excitation light entrance port 290 mounted in the optics configuration panel 136. The excitation light path 289 is directed into the excitation light entrance port 290 by a second excitation path mirror 291, which may be a 45° mirror. The excitation light path 289 enters through the excitation light entrance port 290 towards the excitation monochromator 130 and continues along a path similar to that described above with reference to FIG. 2A.

FIG. 2C also shows an excitation monochromator driver 292, which may be implemented as a stepper motor that drives the monochromator gearwheel 212 (in FIG. 2A) using for example a belt (not shown). FIG. 2C also shows a mirror housing 293 for the first guiding mirror 222 (in FIG. 2A). It is noted that the excitation monochromator driver 292 and the mirror housing 293 may be mounted on the middle plate 168 (in FIG. 1B), which separates the first and second gratings of the excitation monochromator 292 and of the emission monochromator 132.

Figure 2D:
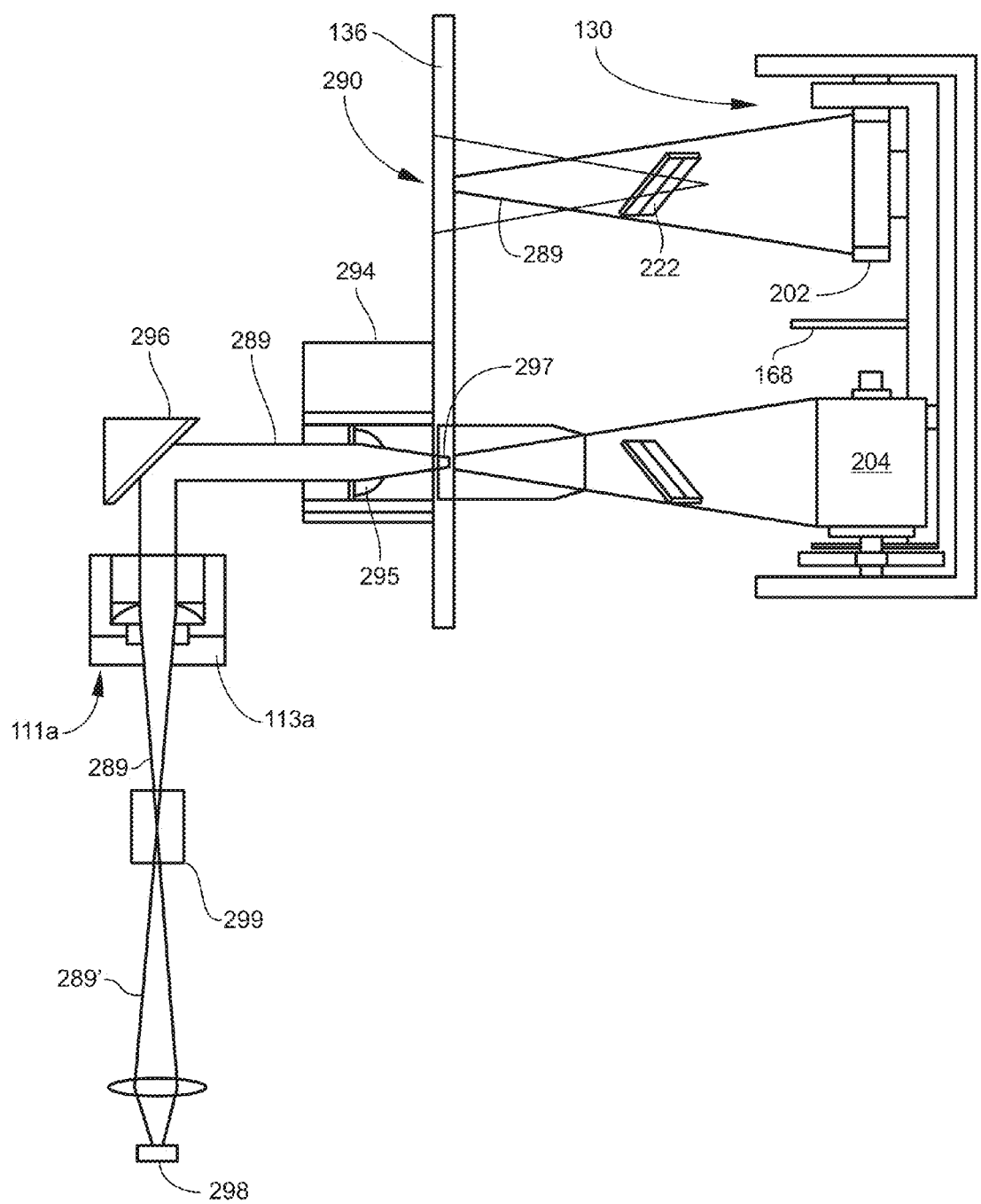
FIG. 2D is a side view of an example excitation monochromator and connecting optics in an example implementation of the system shown in FIGS. 1A and 1B.

FIG. 2D is a side view of the excitation monochromator 130 and connecting optics in an example implementation of the system 100 shown in FIGS. 1A and 1B. FIG. 2D illustrates an example of how the excitation light may be directed in example implementations to a sample. The example illustrated in FIG. 2D is for an excitation light used for absorbance measurements. Examples for performing fluorescence measurements are similar as described below with reference to FIG. 3A.

Referring to FIG. 2D, the excitation light path 289 enters the excitation light entrance port 290 on the optics configuration panel 136, which directs the excitation light path 289 to the first grating 202 of the excitation monochromator 130. The first grating 202 directs the excitation light path 289 towards the first guiding mirror 222 and the second guiding mirror 223 as described above with reference to FIG. 2A. The excitation light path 289 is then guided from the second grating 204 to an excitation light exit port 297 mounted on the optics configuration panel 136.

The excitation light path 289 continues through the excitation light exit port 297 into an excitation connection optics housing 294, which may include a combination of mirrors and/or lenses 295 that directs the excitation light path 289 to align with a path based on a selected detection mode. In the example illustrated in FIG. 2D, the combination of mirrors and/or lenses 295 in the excitation connection optics housing 294 directs the excitation light path 289 to an absorbance excitation path mirror 296. The absorbance excitation path mirror 296 may be mounted in the interface cartridge 104 (FIGS. 1A and 1B), for example, and inserted into the excitation light path 289 for performing absorbance measurements. The absorbance excitation path mirror 296 receives the excitation light on the excitation light path 289 and directs the excitation light downward through the absorbance lens assembly 113a in the first opening 111a in the bottom plate 109. The excitation light is directed through the sample in a well 299 in a microplate that may be mounted on the x-y sample transport 106. A transmitted portion of the excitation light passes through the sample as an emission light along an absorbance emission light path 289'. The emission light is directed along the absorbance emission light path 289' to a light detector 298, such as a photodiode, on the absorbance reader head 117.

B. Detection Mode Selection—Interlace Cartridge

The description of the excitation light path 289 from source to detector provided with reference to FIGS. 2C and 2D relates to using an excitation light for an absorbance measurement. The system 100 may be configured to perform other types of measurements according to different detection modes by combining the functions available with the interface cartridge 104 and the sliding switch mechanism 120 (in FIGS. 1A and 1B). For example, the interface cartridge 104 may be configured to provide optical paths for both excitation and emission (or only emission) light based on a selected detection mode.

In general, for measurements involving an excitation light, the excitation light is directed to the sample on the x-y sample transport 106 underneath the bottom plate 109 (in FIGS. 1A and 1B) of the system 100. Emission light paths are generated from the sample to a selected detector. For any given measurement, a detection mode may be selected using the interface cartridge 104 and an operating mode may be selected using the sliding switch mechanism 120. The interface cartridge 104 and the sliding switch mechanism 120 may be moved to align the excitation light from the desired light source (if an excitation light is required) with the correct path to the sample, and to align the emission light from the sample with the correct path to the selected detector. Added flexibility and diversity of applicability is provided by enabling the use of other application cartridges in place of the interface cartridge 104.

Figure 3A:
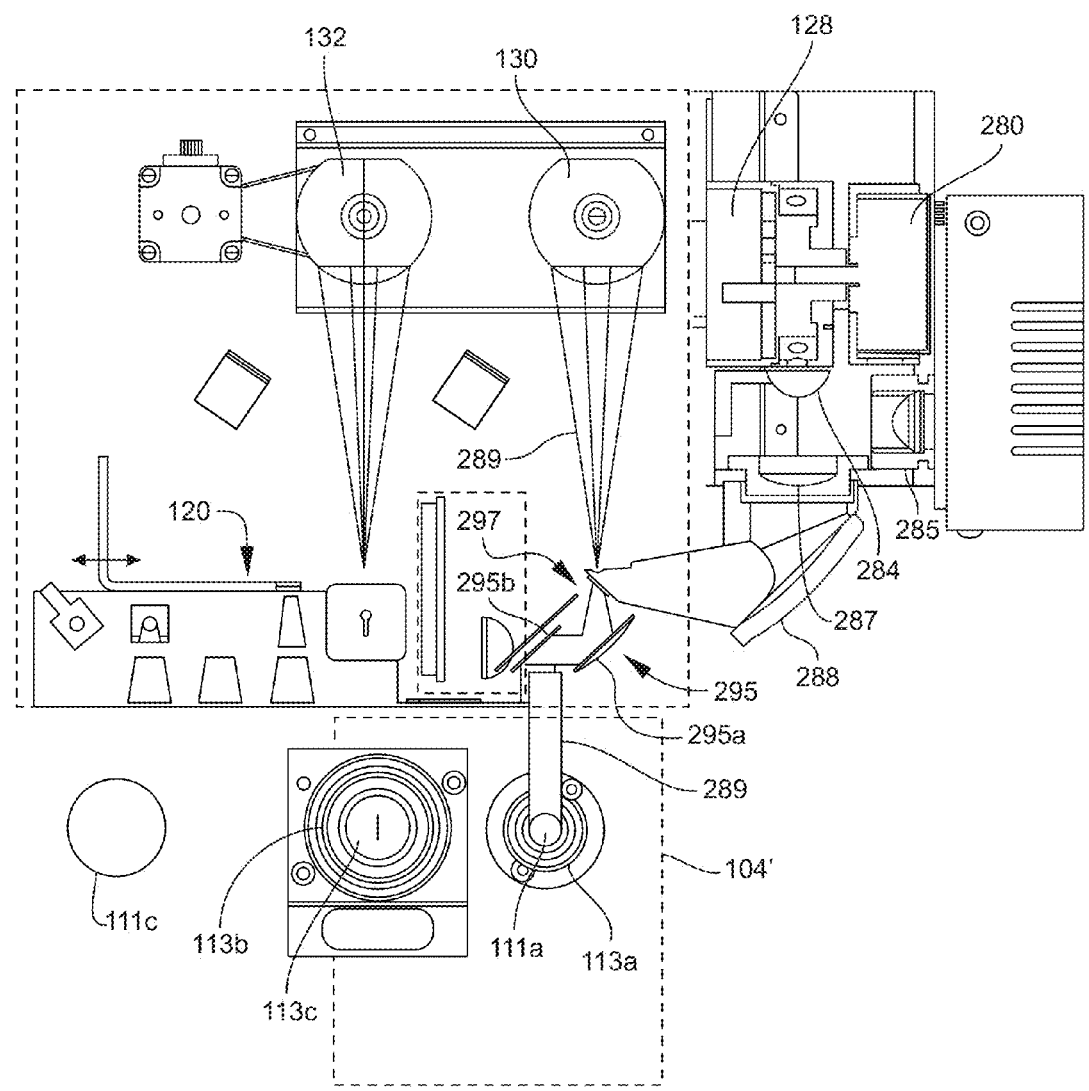
FIG. 3A is a top view of the part of the system shown in FIG. 3A and the bottom plate structure and components under the cartridge carrier.

The interface cartridge 104 provides an interface between the components on a top side of the bottom plate 109 and the sample and components on the bottom side of the bottom plate 109. The components on the top side include light sources and the PMTs as describe with reference to FIGS. 1A-1B and 2A-2D. The components on the underneath side of the bottom plate 109 include the absorbance reader module 117, a bottom fluorescence optics module 115. The interface cartridge 104 is moved according to openings on the bottom plate 109. FIG. 3A is a top view of the part of the system shown in FIG. 3A and the structure of the bottom plate 109 and components under the cartridge carrier 102. FIG. 3A provides a view of the system 100 if the cartridge carrier 102 (and accordingly the interface cartridge 104) is not present.

The example illustrated in FIG. 3A is a light path for an absorbance measurement as illustrated in FIG. 2D. The excitation light path 289 is shown from the excitation monochromator 130 exiting at the excitation light exit port 297 and entering the excitation light connection optics housing 294. The combination of mirrors and lenses 295 in the excitation light connection optics housing 294 may include for example, a parabolic mirror 295a and a polka dot mirror 295b. At the polka dot mirror 295b, the excitation light path 289 may be substantially the same regardless of the type of measurement being taken, although different measurements may use different excitation light sources and may involve different settings of the excitation monochromator 130. The excitation light path 289 reflecting off the polka dot mirror 295b continues to the sample in accordance with the detection mode selected for the measurement.

The system 100 as shown in FIG. 3A provides access to the sample via the three different openings in the bottom plate 109. The detection mode selected for a measurement determines which opening will be used and the interface cartridge 104 (in FIGS. 1A & 1B) is moved to provide the optical path that aligns with the sample through the selected opening. The excitation optical path 289 in FIG. 3A is the same path illustrated in a side view in FIG. 2D for an absorbance measurement. The excitation optical path 289 in FIG. 3A is directed through the absorbance lens assembly 113a aligned with the first opening 111a.

For a fluorescence measurement, the interface cartridge 104 is moved to direct the excitation light path 289 through the top fluorescence/luminescence lens assembly 113b aligned with the second opening 111b. The top fluorescence/luminescence lens assembly 113b and the second opening 111b allows the excitation light path 289 to illuminate the sample below, and to provide access for an emission light path that an emitted light from the sample follows toward a selected light detector. The top fluorescence/luminescence lens assembly 113b aligns with both the excitation light path 289 and the mission light path. A luminescence measurement does not use an excitation light, so for a luminescence measurement the top fluorescence/luminescence lens assembly 113b aligns with only an emission light path.

The third and fourth openings 111c & d in the example implementation illustrated in FIG. 3A may involve measurements of a type that do not involve the interface cartridge 104. For example, the third opening may be used to insert a light guide into the incubation chamber 138 to be in close proximity to the sample to receive emission light in a luminescence measurement. Luminescence measurements typically involve processing samples in reagents or with some added substance that causes the sample to luminesce. In some applications, the luminescence may follow the emission light path through the second opening 111b and top fluorescence/luminescence lens assembly 113b. In applications where the luminescence from samples in neighboring wells in a microplate may create cross-talk, a light guide may be lowered into the third opening 111c in close proximity to the sample of interest. The light guide minimizes the distance through which emitted light is collected from the sample thereby minimizing optical cross-talk, or interfering luminescence from other samples on the sample carrier. The fourth opening 111d in the bottom plate 109 may be used for access by components in the function expander module 108 as described above.

Figure 3B:
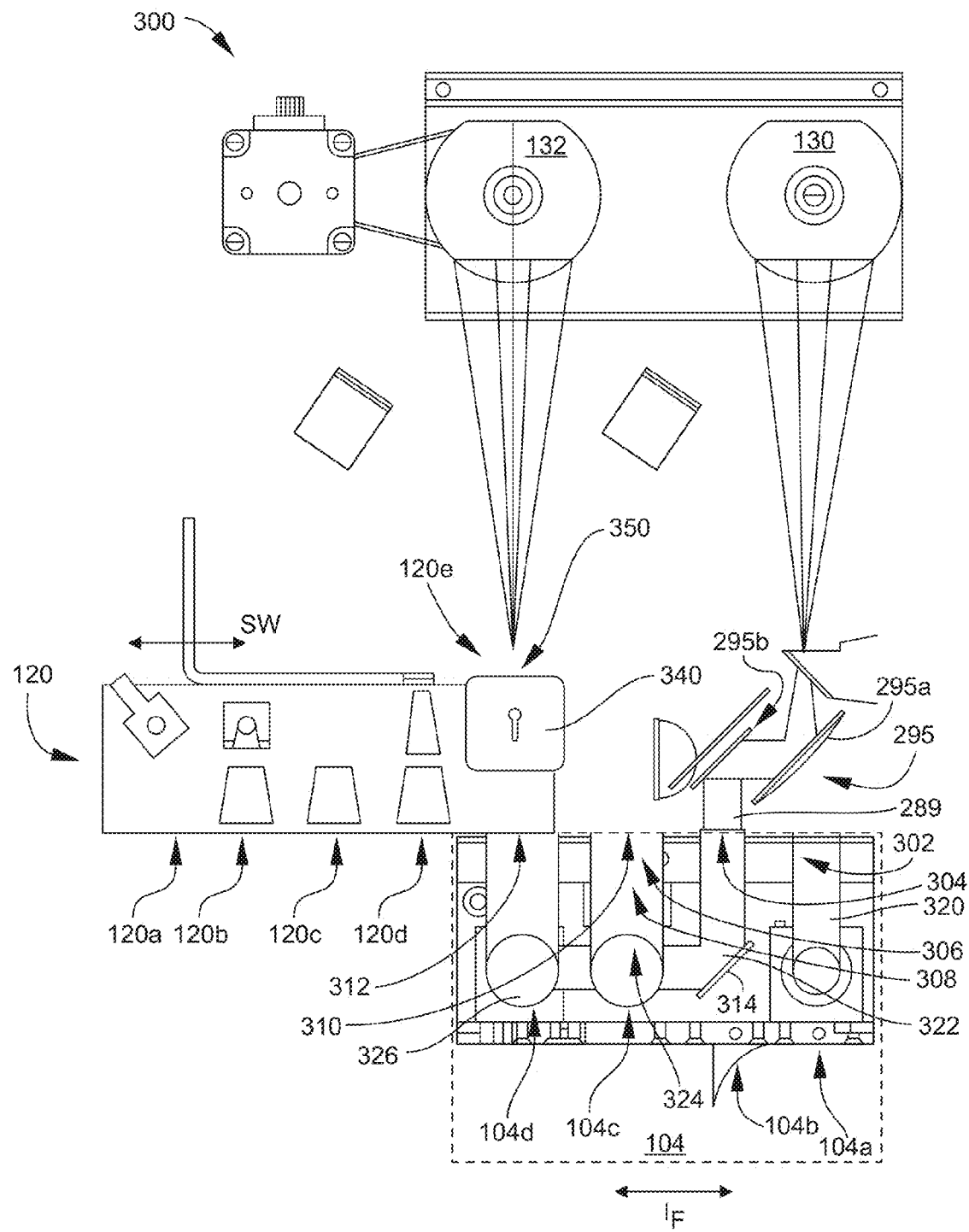
FIG. 3B is a top view of the example implementation of FIGS. 3A-3C and an example implementation of the interface cartridge, the sliding switch mechanism, and the emission monochromator.

FIG. 3B is another top view of the example implementation of FIGS. 1A & 1B and an example implementation of the interface cartridge 104, the sliding switch mechanism 120, and the emission monochromator 132. The top view shown in FIG. 3B includes a portion 300 of the example system shown in FIG. 3A, which includes the excitation monochromator 130, the emission monochromator 132, and the excitation path connection optics 295. The interface cartridge 104 is shown positioned over the openings describe with reference to FIG. 3A.

Figure 3C:
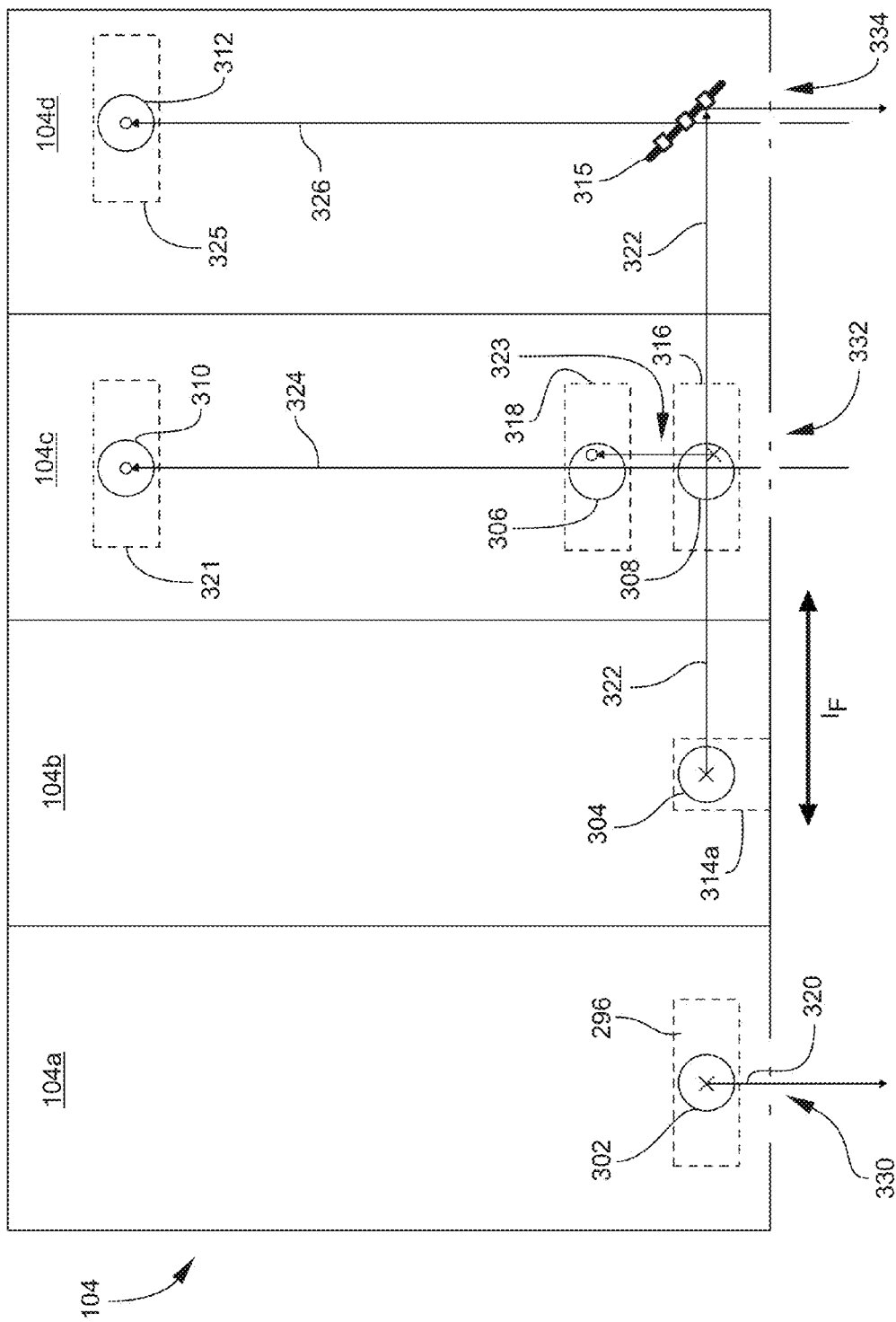
FIG. 3C is a front view of an example implementation of the interface cartridge.

FIG. 3C is a front view of an example implementation of the interface cartridge 104. The vantage point of the front view in FIG. 3C is from that of the excitation monochromator 130 and the emission monochromator 132. FIG. 3C illustrates the access ports for the excitation light path and the emission light path.

Referring to FIGS. 3B and 3C, the interface cartridge 104 may be moved in the direction shown by line $I_F$ in FIG. 3B to set the detection mode for a measurement. Four detection modes are possible in the example implementation in FIG. 3A. The four detection modes are: 1) Absorbance Mode, 2) Fluorescence 1 Mode ("FL1"), 3) Fluorescence 2 Mode ("FL2"), and 4) Luminescence Mode.

The detection mode is selected by moving the interface cartridge 104 in a position that forms an excitation light path and a first part of an emission light path that corresponds to the measurement taken by the selected detection mode. The interface cartridge 104 includes four sections, a first interface cartridge ("IF") section 104a, a second IF section 104b, a third IF section 104c, and a fourth IF section 104d. The four sections 104a, 104b, 104c, and 104d contain optical components configured to form the corresponding light paths.

In the first section 104a, the interface cartridge 104 includes a first excitation light port 302 to permit entry of an absorbance excitation light path 320 towards the absorbance excitation path mirror 296. The absorbance excitation path mirror 296 directs the absorbance excitation light path 320 downward towards the sample as shown in FIG. 3C and as described above with reference to FIG. 2C. In the first section 104a, the interface cartridge 104 also includes a first section bottom port 330 to enable the absorbance excitation light path 320 to extend to the sample when the interface cartridge 104 is moved to align the first section bottom port 330 with the first opening 111a in the bottom plate 109 (in FIG. 3A).

In the second section 104b, the interface cartridge 104 includes a second excitation light port 304 to permit entry of a fluorescence excitation light path 322. The fluorescence excitation light path 322 enters and reflects off a fluorescence light path mirror 314. The fluorescence excitation light path 322 continues parallel to a bottom plane of the interface cartridge 104 to a fluorescence path beam splitter 315, which is mounted in the fourth section 104d of the interface cartridge 104. The fluorescence path beam splitter 315 directs the fluorescence excitation light path 322 downward towards a sample.

In the third section 104c, the interface cartridge 104 includes a third excitation light port 308 to permit entry of a FL2 excitation light path 323. The FL2 excitation light path 323 reflects off a first FL2 mirror 316 in an upward direction (as shown in FIG. 3C) to reflect off a second FL2 mirror 318. The FL2 excitation light path 323 is directed by the FL2 mirror 318 and exits from a fourth excitation light port 306. As described in more detail below with reference to FIG. 4C, the fourth excitation light port 306 aligns with a connector for an optical fiber used to guide the FL2 excitation light path 323 towards optics mounted below the sample to enable a bottom fluorescence measurement.

In the third section 104c, the interface cartridge 104 also includes a third section bottom port 332 to permit entry of a luminescence emission light path 324 from a sample when the third section bottom port 332 is aligned with the second opening 111b in the bottom plate 109 (in FIG. 3A). The luminescence emission light path 324 extends upward in the interface cartridge 104 and reflects off a luminescence path mirror 321 to direct the luminescence emission light path 324 out of the interface cartridge 104 at a luminescence path exit port 310.

In the fourth section 104d, the interface cartridge 104 includes the fluorescence path beam splitter 315 described above in the context of directing the fluorescence excitation light path 322 to the sample. The fluorescence path beam splitter 315 also permits a top fluorescence ("FL1") emission light path 326 generated by the sample to pass upward to a FL1 emission path mirror 325. The FL1 emission light path 326 enters the interface cartridge 104 at a fourth section bottom port 334 when the fourth section bottom port 334 is aligned with the second opening 111*b* in the bottom plate 109 (in FIG. 3A). The FL1 emission path mirror 325 directs the FL1 emission light path 326 out through a FL1 emission path exit port 312.

The optics describe above for each interface cartridge section 104*a-d* configure the excitation light paths and the first part of emission light paths for the type of measurement to be performed. The interface cartridge 104 forms the excitation and emission light paths corresponding to the selected detection mode for the type of measurement. The selected detection mode depends on the position of the interface cartridge 104 relative to a pre-defined main excitation path, a pre-defined main emission path, or both. The main excitation path may be defined as an optical axis aligned with the excitation light path 289 extending from the excitation path optics housing 294 to the interface cartridge 104 as indicated at 289' in FIG. 3B. The main emission path may be defined as an optical axis aligned with a top emission monochromator optical path indicated at 350 in FIG. 3B. Relative to the main excitation path 289' and the main emission path 350 in FIG. 3B, the detection mode for a measurement may be selected by moving the interface cartridge 104 as follows:
 1. Absorbance Mode: Interface cartridge 104 is moved to align the main excitation path 289' with first excitation light port 302 on the first section 104*a* via the combination of mirrors and lenses 295 in the excitation path optics housing 294.
 2. FL1 Mode: Interface cartridge is moved to align the main excitation path 289' with the second excitation entrance port 304 and the main emission path 350 with the FL1 emission path exit port 312.
 3. FL2 Mode: Interface cartridge is moved to align the main excitation light path 289' with the third excitation light port 308 in the third section 104*c*.
 4. Luminescence Mode: Interface cartridge is moved to align the main emission light path 350 with the luminescence path exit port 310.

It is noted that the detection modes listed above are not intended as limiting operation of the system 100 to these modes. In some operating modes, the interface cartridge 104 is not present. In some operating modes, an application cartridge is provided in place of the interface cartridge 104 to provide an emission light generated using different optical paths from the sample not available on the interface cartridge 104. It is also noted that further configurability for different operating modes is possible using the sliding switch mechanism 120.

The different operating modes are selectable according to the position of the sliding switch mechanism 120. The position of the sliding switch mechanism 120 primarily configures the emission light path to a selected detector. In general, the application conducting the measurement relies on a detector in the system 100, such as the PMTs 112 & 114 and the photodiode in the absorbance reader module 117. In the system 100 described herein, the absorbance reader module 117 is mounted under the bottom plate 109. The emission paths configured by the position of the sliding switch mechanism 120 address paths to the PMTs 112 & 114.

The emission light path corresponding to the application performing a measurement may be determined by positioning the sliding switch mechanism 120 according to one of five possible positions. As shown in FIG. 3B, the sliding switch mechanism 120 includes a plurality of positions for directing an optical path in accordance with the selected application.

The sliding switch mechanism 120 may be moved along a direction SW using a motor drive (not shown), such as for example, a linear actuator. The specific mechanism for moving the sliding switch mechanism 120 is not significant; any suitable mechanism may be used. The direction of movement SW may be defined using the sliding switch guide rail 122 (see FIG. 1A).

The sliding switch mechanism 120 in FIG. 3B includes the following positions:
 1. Position A at 120*a*—blocks light to the PMTs 112 and/or 114 when not used in detection; protects the PMTs 112 and 114.
 2. Position B at 120*b*—emission light received from a bottom fluorescence (FL2) measurement via an emission fiber (described below with reference to FIG. 4D) directed to the PMT 112.
 3. Position C at 120*c*—forms light path for upper cartridge light path directly to the first PMT 112 (no emission monochromator path).
 4. Position D at 120*d*—forms light path to direct a) a top interface cartridge light path to the second (optional) PMT 114, b) a lower application (non-interface) cartridge light path to the first PMT 112, c) top and lower application (non-interface) cartridge light paths to the second PMT 114 and the first PMT 112, respectively, and d) a top application (non-interface) cartridge light path to the second PMT 114.
 5. Position E at 120*e*—forms light paths to direct the top interface cartridge light path to the emission monochromator 132 and the lower channel from an application cartridge to the second PMT 114.

It is noted that the sliding switch mechanism 120 in FIG. 3B is in Position E 120*e*. The interface cartridge 104 is shown in position for a top fluorescence reading (FL1). The precise optical path selected for an application depends on the selected position of the sliding switch mechanism 120 and on either the position of the interface cartridge 104, if the interface cartridge 104 is present, or on an application cartridge if one is present. For example, when the sliding switch mechanism 120 is in Position C 120*c* or in Position D 120*d*, the interface cartridge 104 may or may not be present and an application cartridge may be present instead.

C. Operating Mode Selection-Sliding Switch Mechanism

The position of the sliding switch mechanism 120 determines the operating mode of the detection system 100 (FIGS. 1A & 1B), which further determines the emission light path that is used by the application performing a measurement. FIGS. 4A-4F illustrate examples of how the sliding switch mechanism 120 may configure the various emission light paths.

FIG. 4A is a perspective view of an example implementation of the sliding switch mechanism 120. FIG. 4A also includes the emission monochromator 132, which provides a frame of reference for positioning the sliding switch mechanism 120. The sliding switch mechanism 120 in FIG. 4A may be implemented as a structure having optical channels at each selectable position configured to direct light paths through the channels in predetermined directions. The sliding switch mechanism 120 may have an upper level 120' and a lower level 120" to provide selectable optical paths that align with either upper cartridge optical paths or lower cartridge optical paths. The optical channels may be formed as hollowed out compartments in the sliding switch mechanism 120 structure that may contain optical components for directing the light paths. The sliding switch mechanism 120 may also include a hollow conduit for receiving the sliding switch mechanism guide rail 122. In an example implementation, the structure of the sliding switch mechanism 120 may be formed using a metal or other material that provides substantial stability.

The emission monochromator 132 in the system 100 is a dual-level subtracting monochromator similar to the monochromator 200 described with reference to FIG. 2A. The emission monochromator 132 receives an emission light from a sample at a top emission monochromator optical path via the emission monochromator entrance slit 160 (FIG. 1B). The top emission monochromator optical path is aligned with the main emission path 350 described above with reference to FIG. 3B. The top emission monochromator optical path is directed to the top grating 202 of the emission mono chromator, which directs the optical path in a manner similar to the optical path formed in the excitation monochromator 130 as described with reference to FIG. 2A. The bottom grating 204 of the emission monochromator 132 directs a selected wavelength component of the emission light along a lower optical path 420, which passes through the emission monochromator exit slit 162 (FIG. 1B) along a selectable optical path towards a selected one of the PMTs 112, 114.

The sliding switch mechanism 120 in FIG. 4A may be moved to one of the five positions described above, Position A 120a, Position B 120b, Position C 120c, Position D 120d, and Position E 120e, by moving the sliding switch mechanism 120 along the guide rail 122. The sliding switch mechanism 120 is moved relative to a main emission optics housing 402. The main emission optics housing 402 may be a structure that holds optical components, such as a lens 412, configured to align an upper cartridge path to the top emission monochromator path, which is optically aligned with the main emission path 350 and used as a reference for determining the position on the sliding switch mechanism 120 that is selected at any given time. That is, the position of the sliding switch mechanism 120 at a given time is the position aligned with the main emission path 350. It is noted that the main emission optics housing 402 is fixedly mounted in the system 100 by mounting structure that is not shown in FIG. 4A. The main emission optics housing 402 also provides a fixed support for the second PMT 114, which may or may not be used in an example implementation. A lower optics housing 414 may be fixedly mounted under the sliding switch mechanism 120 to provide optical components to direct the lower optical path 420 from the emission monochromator 132 to the first PMT 112.

The movement of the sliding switch mechanism 120 from one position to another according to a desired measurement may be controlled in conjunction with the interface cartridge 104, or with a non-interface application cartridge to complete the desired optical path. Control over the positions of the sliding switch mechanism 120 and the interface cartridge 104 may be provided by a high-level controller configured to control the hardware and software components of the system 100 to operate in accordance with a selected application. Various options for configuring desired optical paths are described below with reference to FIGS. 4B-4F. FIGS. 4B-4F depict the sliding switch mechanism 120 and the interface cartridge 104 with portions of each selectively cut away to illustrate more detail for operation in one of the operating modes of the system. It is to be understood that the examples illustrated are not limiting. The sliding switch mechanism 120 and the interface cartridge 104 may be configured in different ways to achieve different optical paths that may not be illustrated. In addition, alternative optical paths may be configured where the components are located in other positions. For example, a complete hybrid reader that supports all of the possible applications possible with filter-based and monochromator-based readers may be configured differently if backward compatibility with existing applications were not a design goal. In addition, example implementations described herein make advantageous use of an existing form factor provided by the standardized cartridges used for applications to expand the functionality of the existing system that makes use of the existing form factor. In other example implementations, an alternative form factor used in other existing systems may be used, or an alternative form factor that is a brand new design may also be used.

The descriptions of the various options for configuring desired optical paths described below with reference to FIGS. 4B-4F refer to the example implementation of the sliding switch mechanism 120 described with reference to FIG. 4A and an example implementation of the interface cartridge 104 similar to the example described with reference to FIGS. 3B & 3C.

Figure 4B:
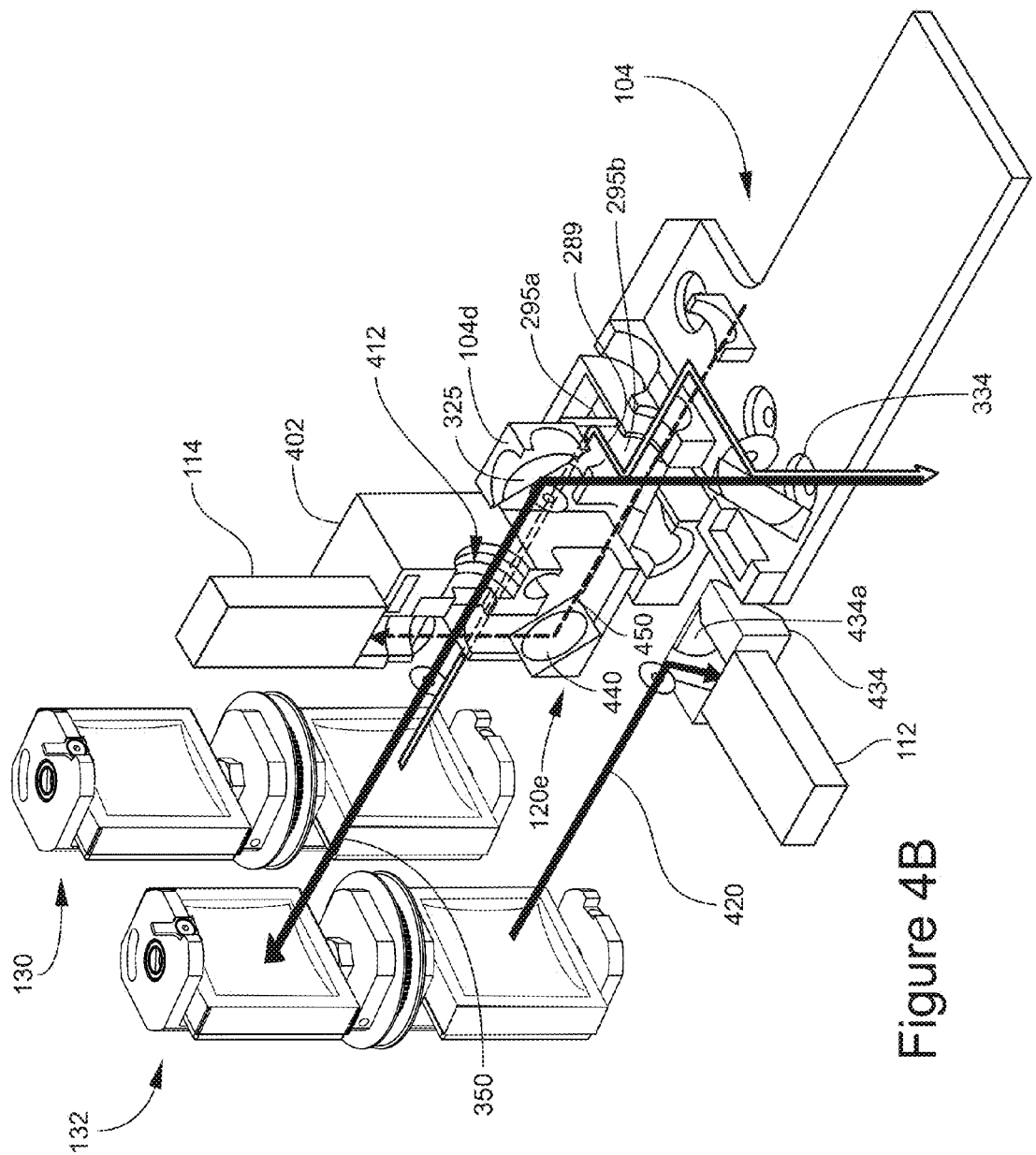
FIG. 4B is a perspective view of the sliding switch mechanism and the interface cartridge illustrating operation of the system according to a first operating mode.

FIG. 4B is a perspective view of the sliding switch mechanism 120 and the interface cartridge 104 illustrating operation of operating modes in one position of the sliding switch mechanism 120. The sliding switch mechanism 120 in FIG. 4B is in Position E 120e. In Position E 120e, an application may perform the following types of measurements:

1. FL1 measurement with interface cartridge 104 in FL1 detection mode.
2. Measurement with second PMT 114 from lower channel optical path from application cartridge; e.g. Paradigm® luminescence cartridge with lower channel exit.
3. Luminescence measurement with interface cartridge 104 in Luminescence mode.

For the FL1 measurement, the interface cartridge 104 is moved to select the FL1 mode as described above with reference to FIGS. 3A-3C. The FL1 mode aligns the main excitation path 289' with the first excitation light port 302 on the first section 104a of the interface cartridge 104 via the combination of mirrors and lenses 295 in the excitation path optics housing 294. The excitation light is directed along the fluorescence excitation light path 322 to the sample. The emitted light from the sample follows an emission light path to the FL1 emission path mirror 325, which aligns the emission light path with the main emission path 350. The emitted light is processed by the emission monochromator 132 according to the specifications of the application performing the measurement. The emitted light exits the emission monochromator 132 along the lower optical path 420, which directs the emitted light to a main detector optics housing 434 containing optics components such as for example, a detector mirror 434b, that direct the emitted light to the first PMT 112. The first PMT 112 measures the light intensity of the emitted light.

The second type of measurement with the sliding switch mechanism 120 in Position E 120e is performed for an application cartridge that generates an emitted light at a lower channel exit to form a lower emission light path 450. The sliding switch mechanism 120 at Position E 120e includes optical components in a lower portion of the sliding switch mechanism 120. In FIG. 4B, Position E 120e of the sliding switch mechanism 120 includes a mirror 440 mounted in the lower portion of the Position E 120e of the sliding switch mechanism 120. The mirror 440 directs the lower emission light path 450 upward through a channel and lens to the second PMT 114. In an example implementation, the second PMT 114 may be a UV/VIS PMT. A special cartridge, such as a Paradigm® luminescence cartridge with a lower exit or dual-channel luminescence application. One example of such an application cartridge for bioluminescence resonance energy transfer ("BRET") assays.

The third type of measurements that may be taken with the sliding switch mechanism 120 in Position E 120e may be performed for luminescence measurements with the interface cartridge 104 in the Luminescence mode at position 104c. The luminescence from the sample is directed up in the third section 104c of the application cartridge 104 to the luminescence path mirror 321 (not shown in FIG. 4B, see FIG. 3C). The luminescence path mirror 321 directs the emitted luminescence to align with the main emission path 350. The sliding switch mechanism 120 at Position E 120e directs the main emission path 350 to the emission monochromator 132 for measurement by the first PMT 112.

Figure 4C:
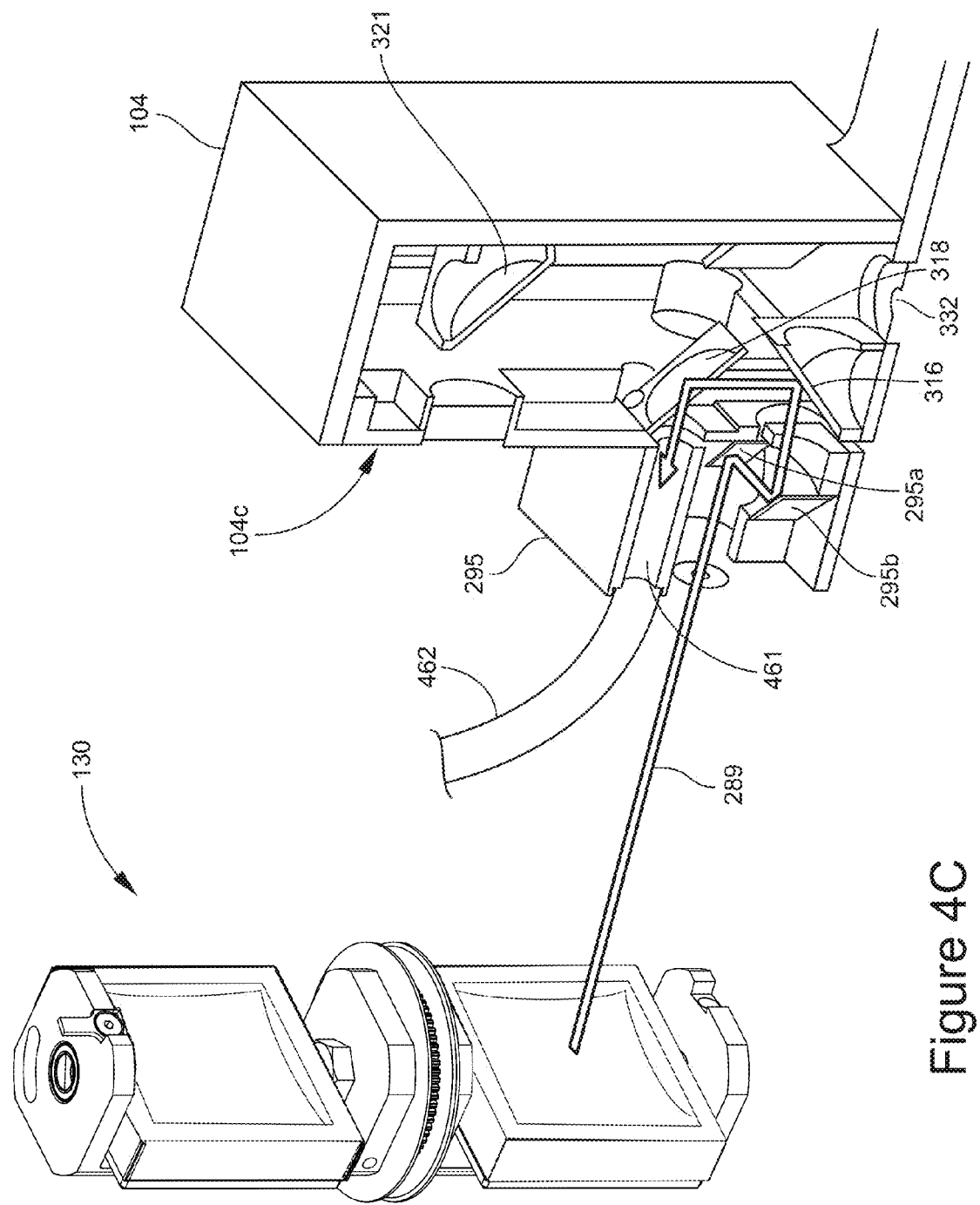
FIG. 4C is a perspective view of the interface cartridge in a selected detection mode position to receive an excitation light from the excitation monochromator for connection to an excitation fiber.
Figure 4D:
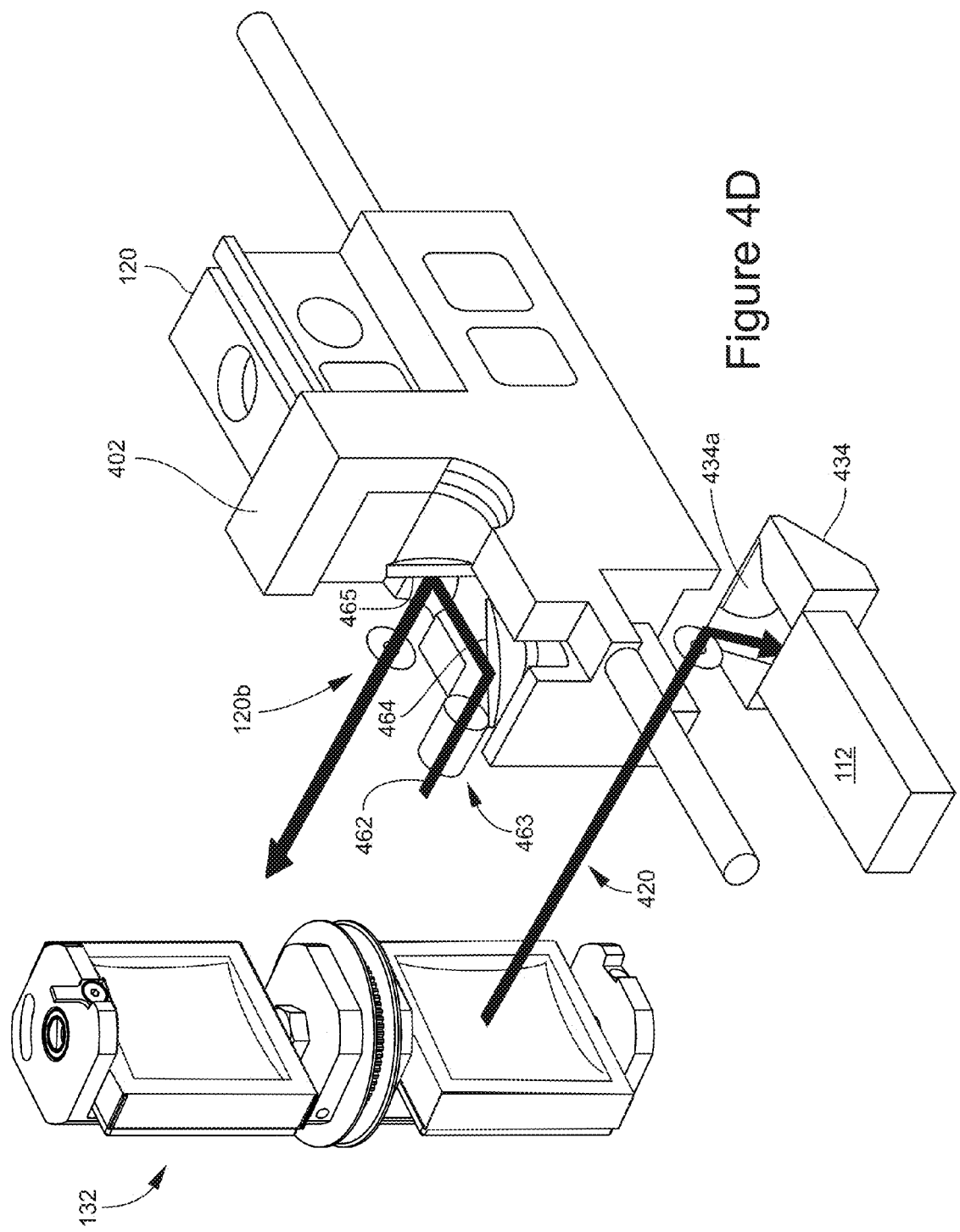
FIG. 4D is a perspective view of the sliding switch mechanism in a bottom measurement position for receiving an emission light from an emission fiber according to another operating mode.

FIGS. 4C and 4D are perspective views of the interface cartridge 104 in a bottom fluorescence excitation position and the sliding switch mechanism 120 in Position B 120b for performing bottom fluorescence measurements. The interface cartridge 104 is positioned at the third section 104c to align the fluorescence excitation light exiting from the polka dot mirror 295b in the excitation connection optics housing 294 with the third excitation light port 308, which provides access to the first FL2 mirror 316. The first FL2 mirror 316 reflects the excitation light to the second FL2 mirror 318, which directs the excitation light out the fourth excitation light port 306 to an excitation fiber connector 460. An excitation fiber 462 carries the excitation light to the bottom fluorescence optics module 115. The bottom fluorescence optics module 115 directs the excitation light up to the sample through the bottom of the sample well. The emitted light from the sample is received at the bottom fluorescence optics module 115, which directs the emitted light through an emission fiber 461. The emission fiber 461 carries the emitted light to an emission fiber connector 463 (in FIG. 4D), which directs the emitted light to a parabolic mirror 464 in the optical channel formed in Position B 120b. The parabolic mirror 120b directs the emitted light to a collimating off-axis mirror 465. The collimating off-axis mirror 465 aligns the emitted light with the main emission path 350. The emitted light continues to follow the lower optical path 420 for measurement by the first PMT 112.

Figure 4E:
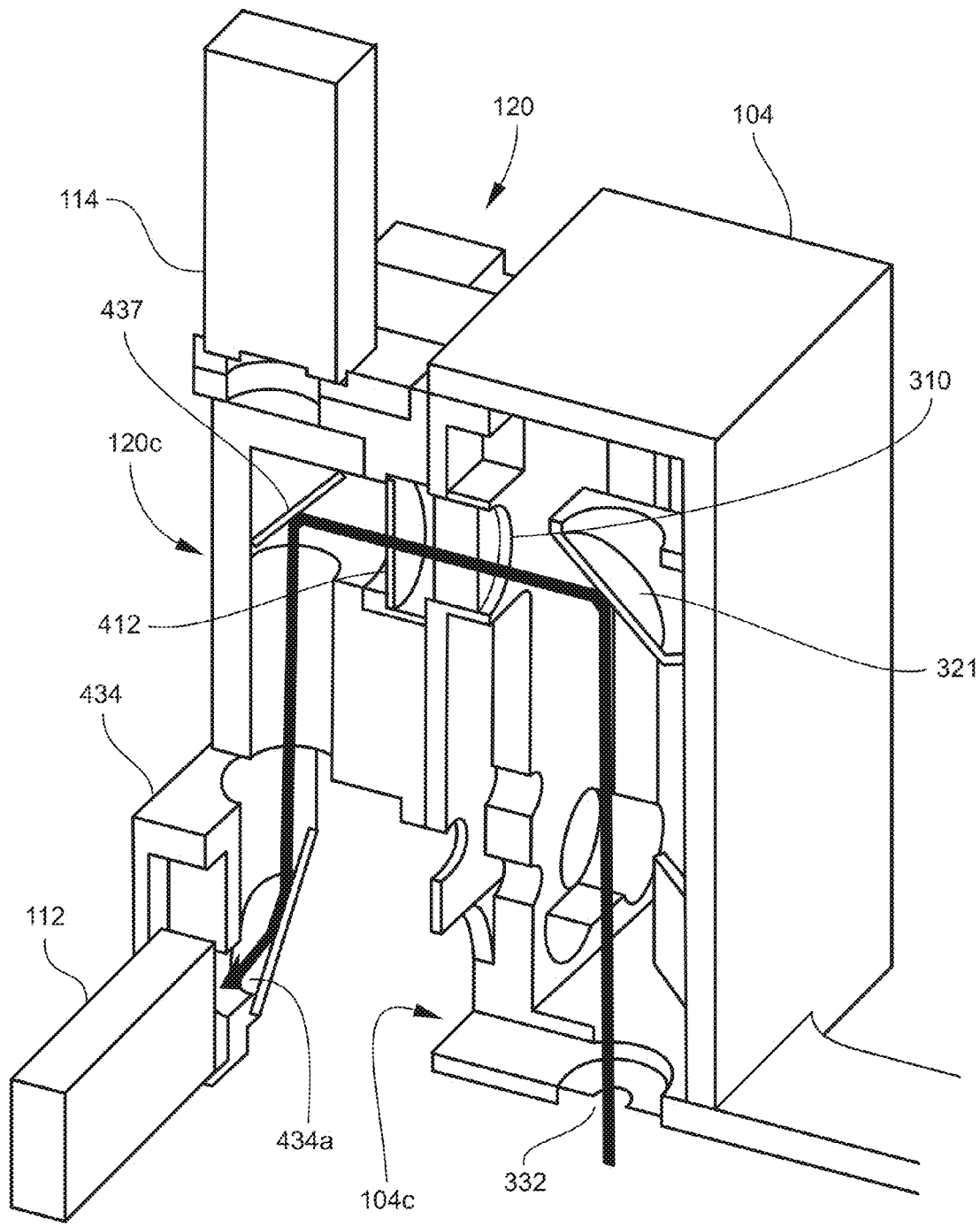
FIG. 4E is a perspective view of the sliding switch mechanism illustrating operation of the system according to another operating mode.

FIG. 4E is a perspective view of the sliding switch mechanism 120 in another position of the sliding switch mechanism 120. In Position C 120c, an application may perform the following types of measurements:

1. Luminescence measurement with interface cartridge 104 in the luminescence detection mode at position 104c.
2. Measurement at the first PMT 112 from upper channel optical path from an application cartridge; e.g. Paradigm® cartridge with upper channel optical path for fluorescence measurement.

For the luminescence measurement with the interface cartridge 104 in the luminescence detection mode 104c, the sliding switch mechanism 120 in Position C 120c receives the luminescence emission light directed from the luminescence path mirror 321 through the lens 412 in the main emission optic housing 402. The Position C 120c housing includes a mirror 437 to direct the luminescence emission light to the first detector 112. The luminescence emitted light is directed to the first PMT 112 without processing by the emission monochromator 132.

For the measurement from the upper channel optical path from an application cartridge, the application cartridge and not the interface cartridge 104 provides an emitted light from a sample along an optical axis aligned with the main emission path 350. In an example implementation, a fluorescence emission light from an application cartridge supporting an upper channel path may be measured directly by the first PMT 112.

Figure 4F:
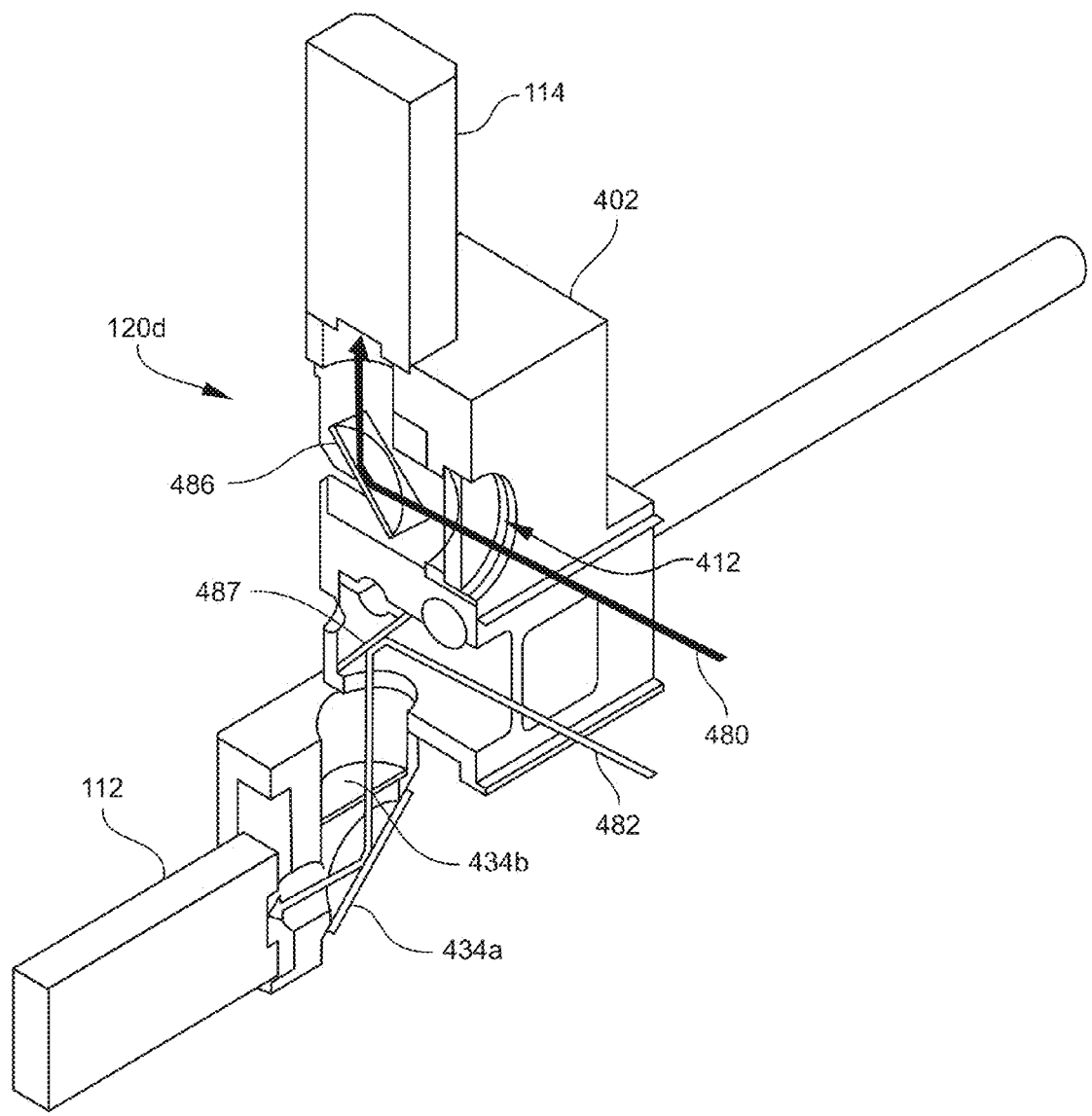
FIG. 4F is a perspective view of the sliding switch mechanism in position to direct the top luminescence emission path of the interface cartridge or an upper cartridge path from an application cartridge to the specialized PMT.

FIG. 4F is a perspective view of the sliding switch mechanism 120 in Position D 120c. In Position D 120d, an application may perform the following types of measurements:

1. Luminescence measurement with second PMT 114 with interface cartridge 104 in Luminescence detection mode at position 104c.
2. Measurement at first PMT 112 from lower channel optical path from application cartridge; e.g. Paradigm® fluorescence applications.
3. Measurement at first PMT 112 and second PMT 114 from lower channel optical path and upper channel optical path from application cartridge with dual emission paths; e.g. Paradigm® fluorescence applications.

For the luminescence measurement with the second PMT 114 and the interface cartridge 104 in the luminescence detection mode at position 104c, the luminescence emission light following an upper channel optical path 480 from a sample may be directed from the luminescence path mirror 321 (shown in FIG. 4E) to align along the main emission path 350. The sliding switch mechanism 120 at Position D 120d includes a mirror 486 that directs the luminescent emitted light up to the second PMT 114.

For the measurement at the first PMT 112 from a lower channel optical path 482 provided by an application cartridge as opposed to the interface cartridge 104 (e.g. Paradigm® fluorescence application cartridge with lower emission channel), the sliding switch mechanism 120 Position D 120d includes a second mirror 487 that directs the emitted light down to the detection mirror 434b in the main detector optics housing 434, which directs the emitted light to the first PMT 112.

For the measurement at the first PMT 112 and second PMT 114, an application cartridge with dual emission paths directs the emitted light along the upper channel optical path 480 and the lower channel optical path 482 for measurement by the first PMT 112 and the second PMT 114 as described above for the other two measurement types.

D. Optical Configuration Panel

Figure 5:
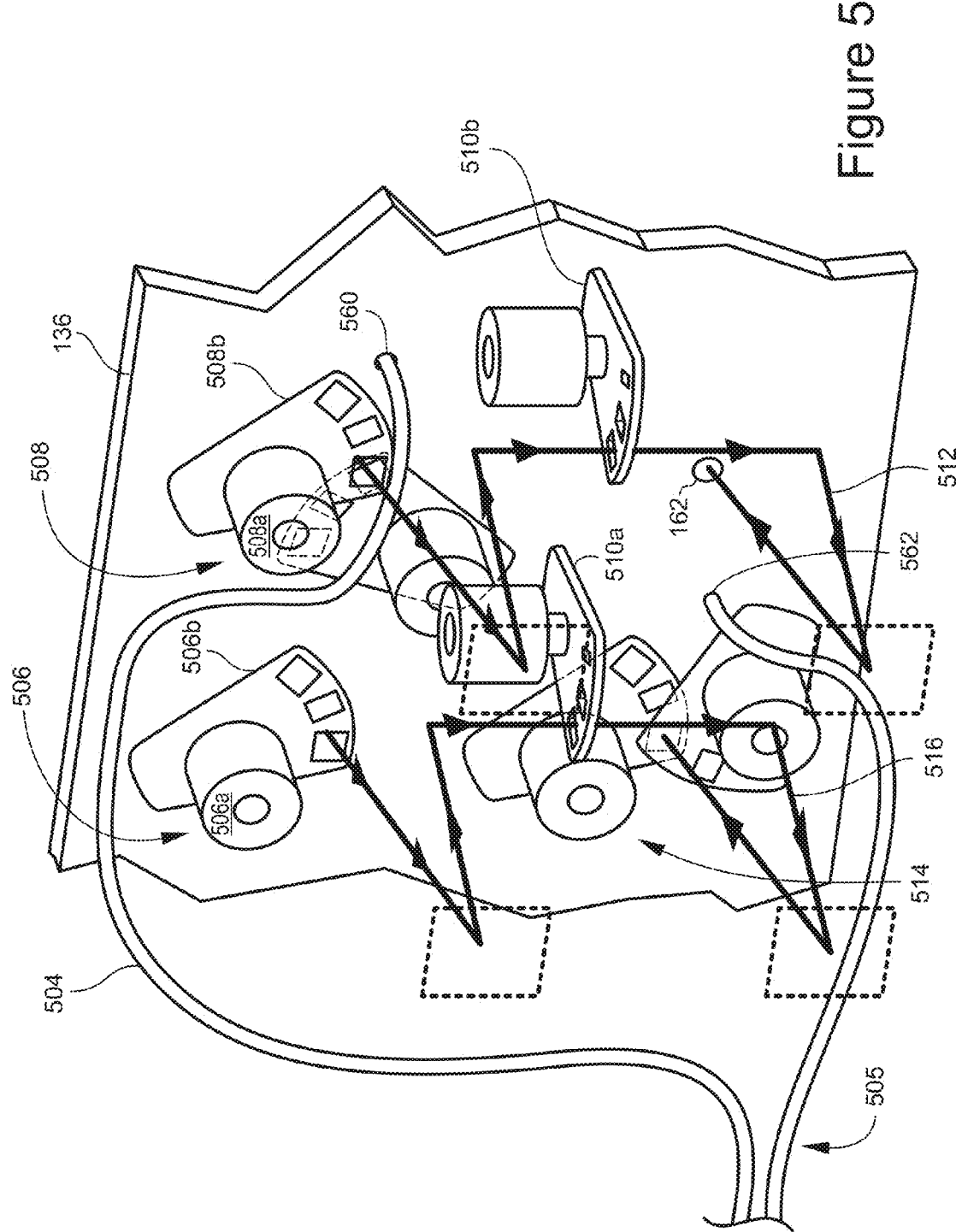
FIG. 5 is a perspective view of an example implementation of the optical configuration panel shown in FIGS. 1A and 1B.

FIG. 5 is a perspective view of an example implementation of the optical configuration panel 136 shown in FIGS. 1A and 1B. The optical configuration panel 136 includes optical components such as mirrors and filters that direct and/or condition the excitation and/or emission light paths in accordance with a selected application. As shown in FIGS. 1A and 1B, the optical configuration panel 136 is positioned between the sliding switch mechanism 120 and the monochromators 130, 132. The components on the optical configuration panel 136 may condition the optical paths as excitation and/or emission paths depending on the application and component.

The optical configuration panel 136 in FIG. 5 includes a bottom emission fiber 504, an excitation path entrance slit toggle switch 506, an emission path entrance toggle switch 508, first and second middle switches 510a, 510b, a bottom excitation fiber 505, an excitation path exit toggle switch 514, and the emission path exit port 162. The components on the optics configuration panel 136 are controlled to condition light paths in an excitation double monochromator light path 510 and an emission double monochromator light path 512. The view of FIG. 5 is understood to be from the perspective of position within a chamber containing the monochromators. For the view in FIG. 5, the sliding switch mechanism 120 and interface cartridge 104 and other components are located on the other side of the optics configuration panel 136.

Optical components on the other side of the optics configuration panel 136 may be used to direct the light source excitation light from either the LED wheel 128 or the flash lamp module 110 to the excitation light entrance port 160 mounted on the optics configuration panel 136 as described above with reference to FIGS. 1A and 1B. The excitation light entrance port 160 may include the excitation path entrance slit toggle switch 506. Different entrance slit configurations may be selected using the excitation path entrance slit toggle switch 506. Similarly, the emission path entrance slit toggle switch 508 may be positioned at the entrance port for the emission light path.

The excitation path entrance slit toggle switch 506 and the emission path entrance slit toggle switch 508 may be implemented as toggle switches that include a toggle switch motor 506a, 508a and multiple slit position rack 506b, 508b. The multiple slit position racks 506b, 508b may be configured to have up to four positions, each of which may have a different filter or slit to allow adjustment of the light path to different bandwidths and to permit the use of order sorting filters and polarizing filters. The multiple slit position racks 506b, 508b are moved from one position to the next using the toggle switch motor 506a, 508a. The toggle switch motors 506a, 508a may be implemented using an 18° stepper motor. Two hard stops are included on the multiple slit position racks 506b, 508b for precise positioning, and to provide a shield to make sure that there is no light leakage through the housing of the toggle switches 506, 508.

In an example implementation, the excitation path entrance slit toggle switch 506 may be configured to switch one of 3 different entrance slits. The emission path entrance slit toggle switch 508 may be configured to switch two pairs of different slits where one pair is switched in combination with an order sorting filter. The first middle slit toggle switch 510a switched in to the excitation light path may include three different middle slits plus an optional filter. The second middle slit toggle switch 510b may include two different middle slits. The excitation path exit slit toggle switch 514 may include three different order sorting filters plus one filter for special applications, and a polarizing filter plus two neutral density filters. The first middle slit toggle switch 510a and the second middle slit toggle switch 510b may be implemented using a motor and multiple slit position rack in a manner similar to the excitation path entrance slit toggle switch 506 and the emission path entrance slit toggle switch 508.

The toggle switches and combinations of optical components may permit support for different bandwidths with the excitation monochromator 130 and emission monochromator 132. The use of gratings in $2^{nd}$ order for deep UV absorbance by be supported by adjusting the slits to the wavelength dispersion of the $2^{nd}$ order. Dynamic extension of PMT measurements may be supported using neutral density filters to change the light intensity of the flash lamp in rapid fashion. Standard PMT in analog mode may be used if needed due to the use of a flash lamp as a light source and the use of photon counting if possible.

The optics configuration panel 136 may also include a first fiber connection 560 for a bottom emission fiber 504, which may extend from the panel 136 to the bottom optics for fluorescence measurements. The first fiber connection 560 may be aligned with the emission fiber connector 460 that connects the emission fiber 504 light path to the sliding switch mechanism 120 as shown in FIG. 4D. The optics configuration panel 136 in FIG. 5 also includes a second fiber connection 562 to attach a bottom excitation fiber 505, which may extend from the panel 136 to the bottom optics for fluorescent measurements as described with reference to FIGS. 4C and 4D. The second fiber connection 562 may be aligned with the excitation fiber port 461 that connects the excitation fiber path to the excitation light optics as shown in FIG. 4D.

E. Function Expander

Figure 6A:
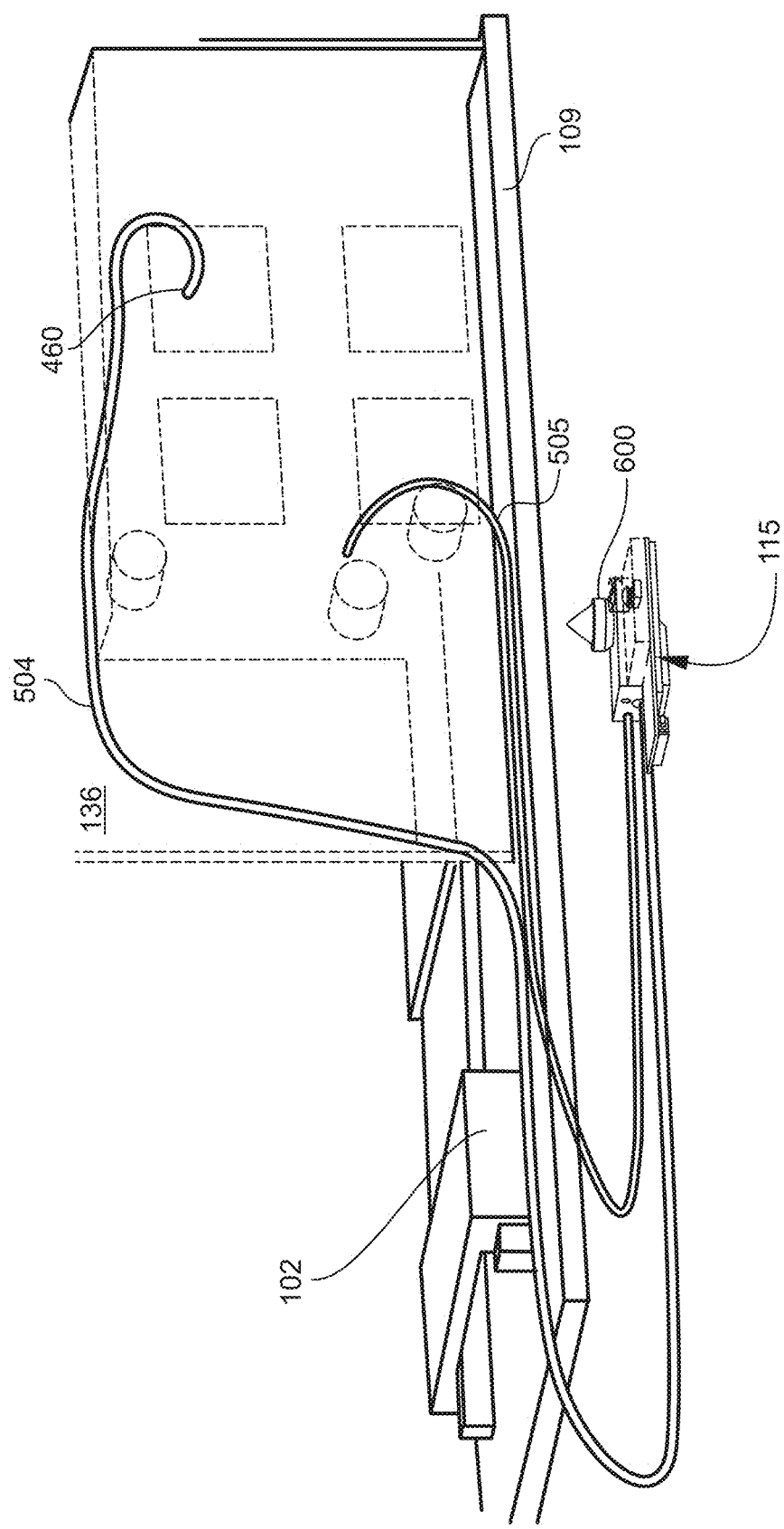
FIG. 6A is a perspective view of an example implementation of the system described with reference to FIGS. 1A and 1B and an example location for the function expander board.

FIG. 6A is a perspective view of an example implementation of the system described with reference to FIGS. 1A and 1B illustrating an example location for bottom fluorescence optics module 115. The system 100 as shown in FIG. 6A includes the optics configuration panel 136, the cartridge carrier 102, and the bottom plate 109. The bottom fluorescence optics module 115 includes a bottom fluorescence read head 600. The bottom fluorescence optics module 115 is positioned below the bottom plate 109 with space between the bottom fluorescence optics module 115 and the bottom plate 109 sufficient for providing a microplate carrier 602. The bottom fluorescence optics module 115 is positioned to permit the bottom fluorescence read head 600 to take bottom readings of the samples in the microplate carrier 602. FIG. 6A shows the bottom emission fiber 504 and the bottom excitation fiber 505 extending from the optics configuration panel 136 and the bottom fluorescence optics module 115.

Figure 6B:
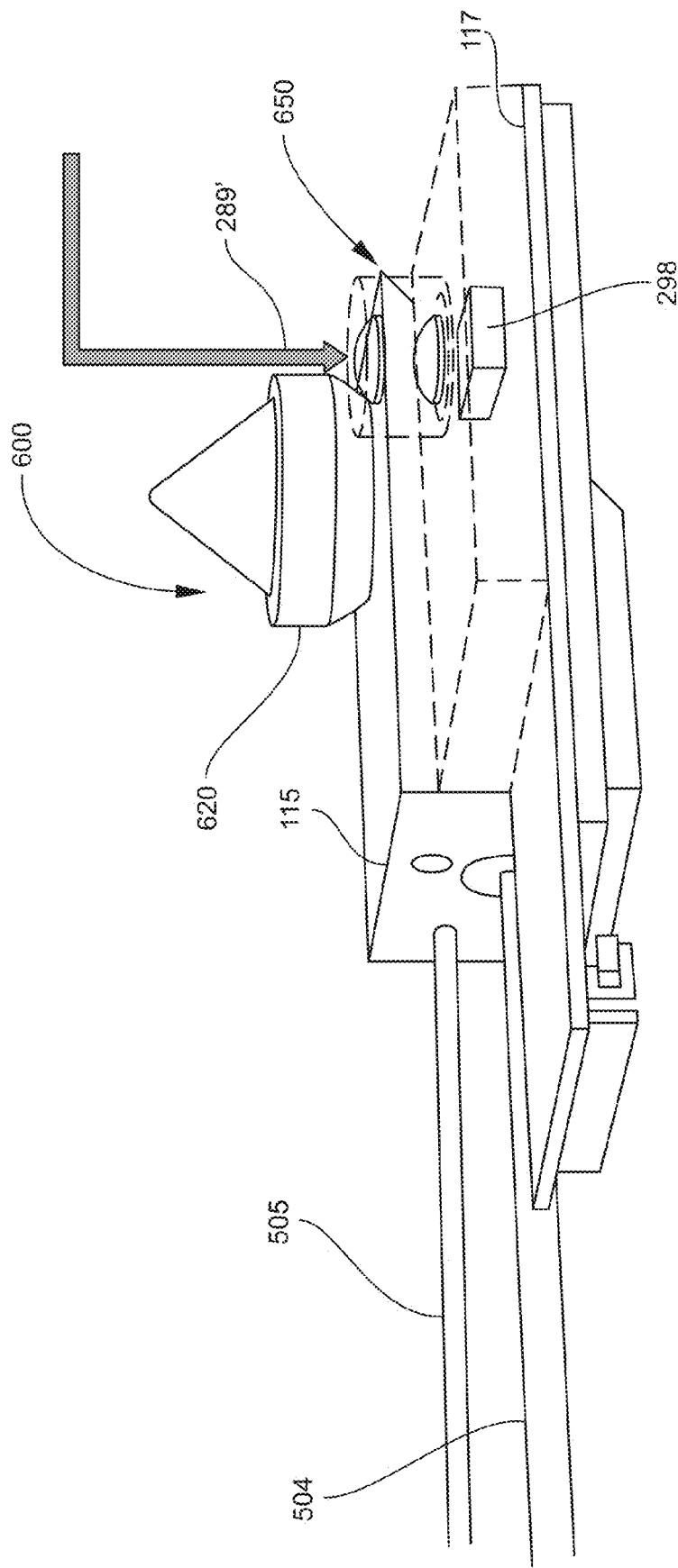
FIG. 6B is a perspective view of the absorbance measurement reading components on the function expander board.

FIG. 6B is a perspective view of the absorbance measurement reading components on the absorbance read head 117 and the bottom fluorescent measurement components on the bottom fluorescence optics module 115. As shown in FIG. 6B, the bottom fluorescent measurement components include the bottom fluorescence read head 600, which may include an objective lens 620, for use with a monochromator and connections for the emission fiber 504 and the excitation fiber 505. The bottom fluorescence read head 600 performs the fluorescence reading from below the sample. The absorbance measurement reading components includes an absorbance detection board 650, which may include a photodiode 298, local amplification and an A/D converter.

III. Cell Imaging System Interface

Figure 7:
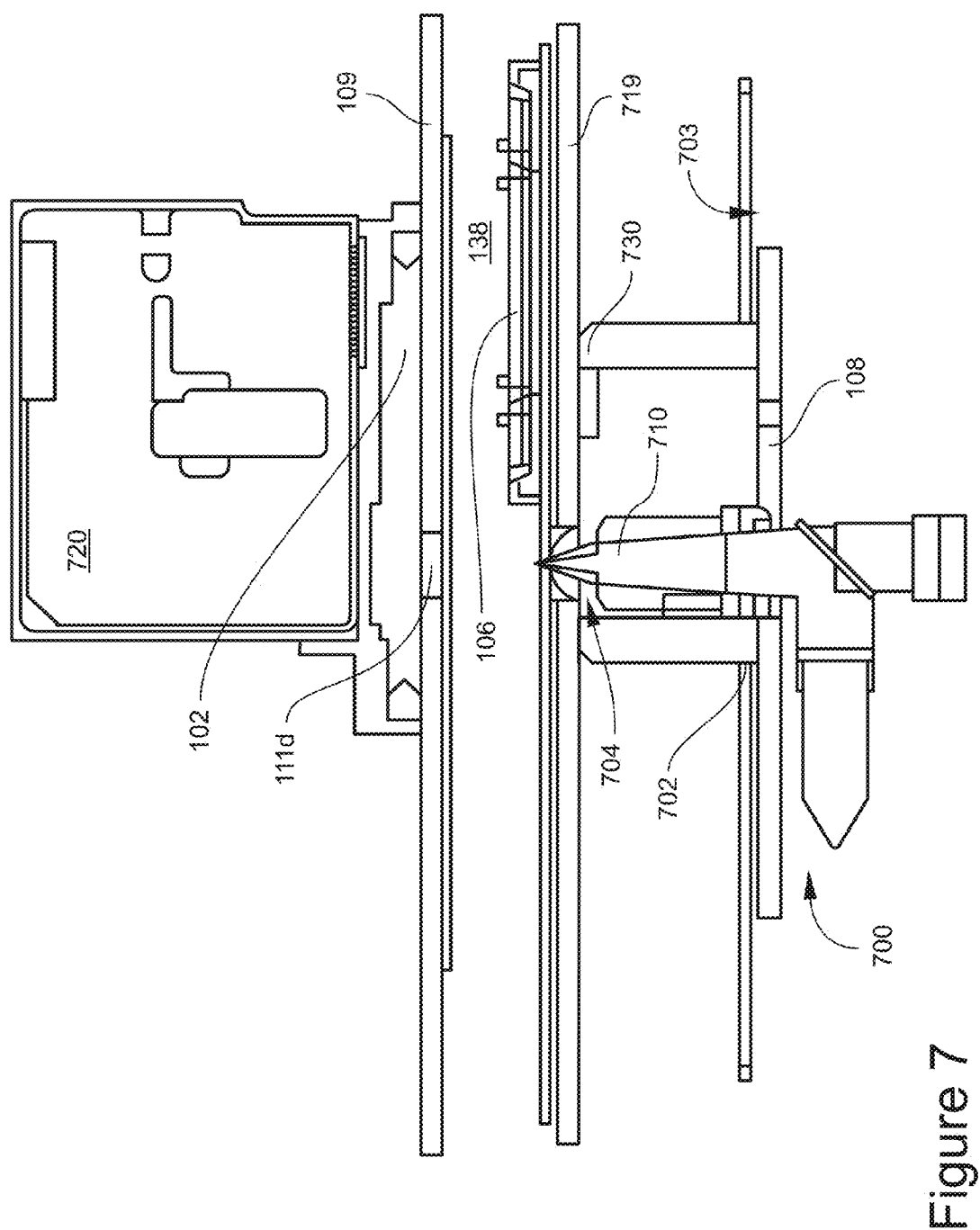
FIG. 7 is a side view of the imaging interface board connected for use as an interface for an imaging system.

FIG. 7 is a side view of the function expander module 108 connected for use as an interface for an imaging system 700. In example implementations, the system 100 may be mounted on top of a cell imaging system at an imaging system interface 710 to use resources of the system 100 to enhance the functionality of the cell imaging system. The interface for the imaging system 700 includes a first opening 702 in a bottom system chassis plate 703 of the system 100. The imaging system interface 710 is fitted into the first opening 702 to extend into a second opening 704 in an incubation chamber bottom 719. An imaging system/reader interface board 730 may be mounted under the incubation chamber bottom 719. The imaging system/reader interface board 730 includes electronics for providing any control signals that may be exchanged between the reader system 100 and the imaging system 700. The second opening 704 is aligned with the bottom plate opening 111d in the bottom plate 109 of the system 100. The system 100 is shown as including the cartridge earner 102 supporting a cell imaging cartridge 720.

The cell imaging cartridge 720 may be a specially developed cell imaging application cartridge. For example, the cell imaging cartridge 720 may be an injecting cartridge that includes reagent injecting functions or an illuminating cartridge that includes imaging illumination functions. The injecting functions may be performed through the bottom plate opening 111d with the microplate carrier 106 positioned below the opening to receive injection of reagents or other liquids in accordance with the cell imaging application. The injector cartridge may be used for flash type luminescence measurements (in applications that do not include the cell imaging systems) or to support cell imaging system applications where a cell stimulus needs to be added during measurement time, or just before measurement time. The illumination function may be performed through the same bottom plate opening 706 using a light source in the cell imaging cartridge 720. The light source path may be directed through the bottom plate opening 706 for use by the cell imaging system at the imaging system interface 710.

The combination of the system 100 with the cell imaging system may allow the cell imaging system to perform cell measurements using epifluorescence. In addition, the imaging system may be able to perform white light imaging using dark field illumination from the bottom. The enhanced illumination and injection features describe above may also expand the functionality of the cell imaging system.

Figure 8:
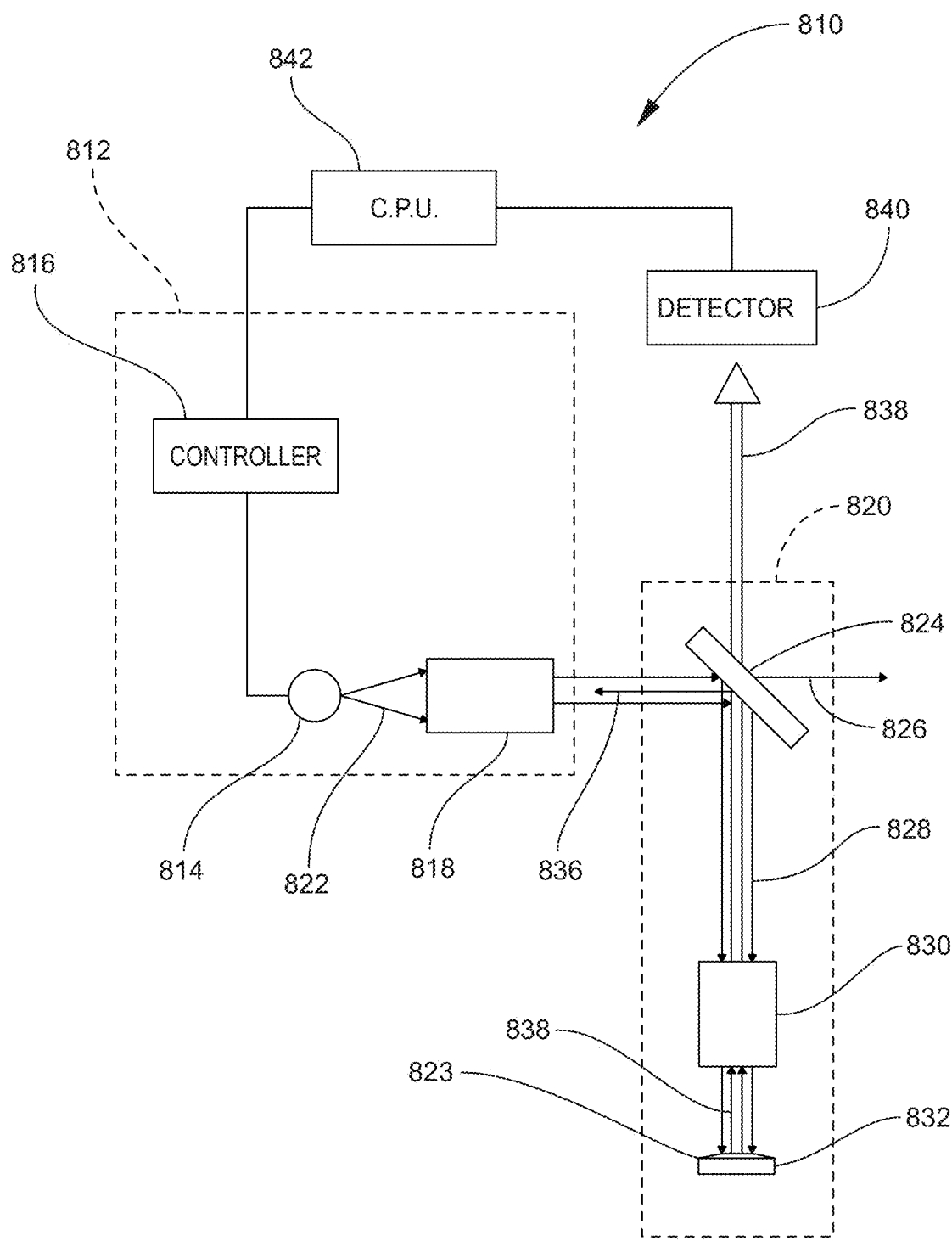
FIG. 8 is a schematic diagram of an example of a fluorescent microscopy system that may be used with the monochromator-based and filter-based multimode reader illustrated in FIGS. 1A and 1B.

With respect to performing measurements based on epifluorescence, a cell imaging system may be provided to operate with the system 100 more efficiently. FIG. 8 is a schematic diagram of an example of a fluorescent microscopy system 810 that may be used with the monochromator-based and filter-based multimode reader illustrated in FIGS. 1A and 1B. The fluorescent microscopy system 810 includes a controller 842, a dye excitation apparatus 812, a microscope 820, and a detector 840. The dye excitation apparatus 812 may include a controller 814, a light source 814, and an optical system 818. The dye excitation apparatus 812 may be implemented as a cartridge for use in the system 100 via the cell imaging interface 710 described above with reference to FIG. 7.

The optical system 818 in the dye excitation apparatus 812 may direct emitted light 822 from the light source 814 as an excitation beam 828 having a distribution of light flux suitable for simultaneously illuminating substantially all of the field of view of the microscope 820. A dichroic mirror 824 in the microscope 820 reflects excitation beam 828 onto an objective lens 830 of the microscope 820. Any light 826 above the pre-selected wavelength passes through the dichroic mirror 824. The objective lens 830 focuses the excitation beam 828 onto a specimen 832. The specimen 832 is prepared to contain fluorescent dye 823. The specimen 832 fluoresces in response to the excitation beam 828 and emits light 838, which passes through the dichroic mirror 824 and is detected by the detector 840. Any scattered and reflected light 836 below a cutoff frequency is reflected by dichroic mirror 824. The controller 842 processes the output of the detector 840 and interfaces with the electronic controller 816.

Figure 9A:
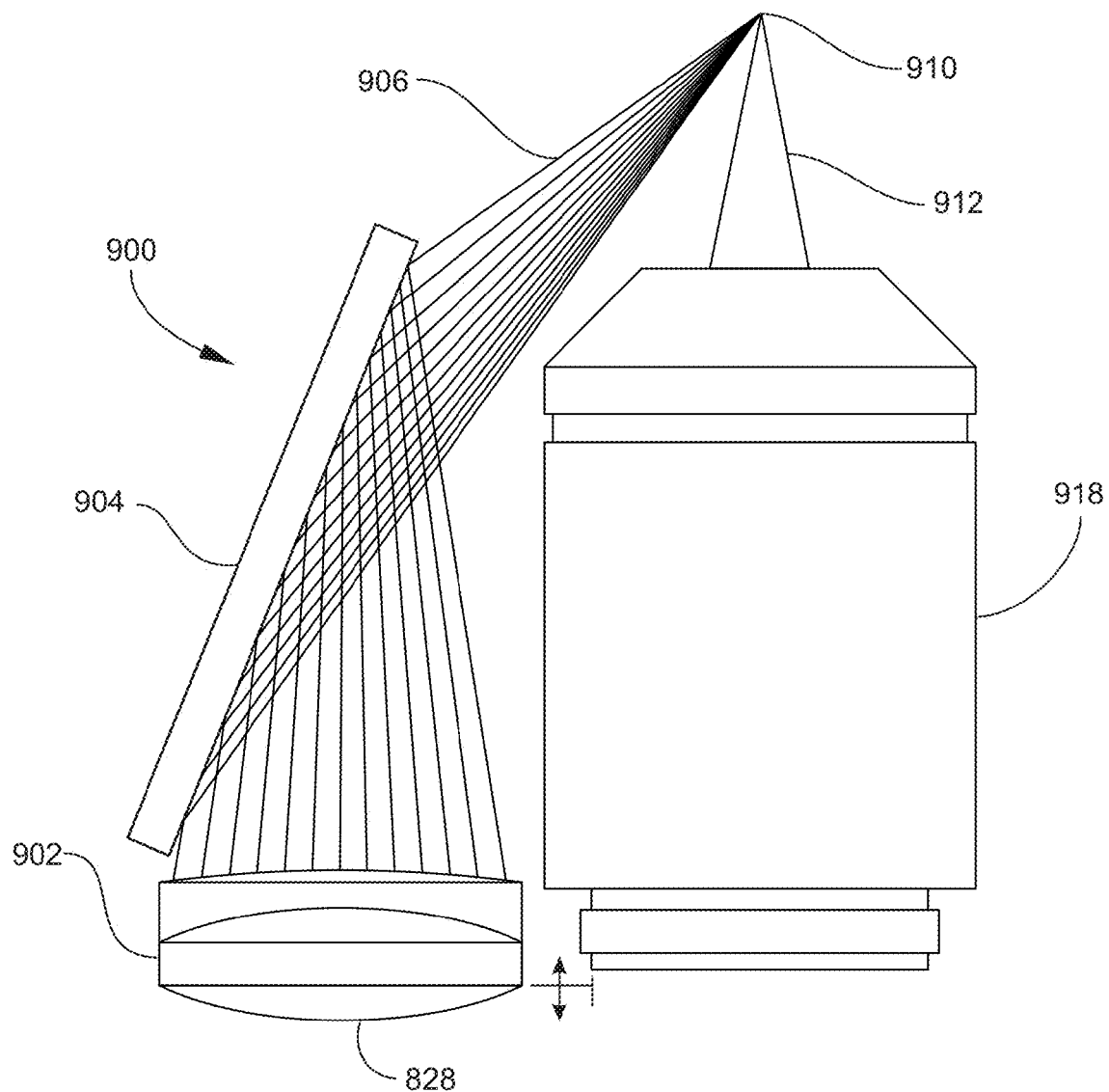
FIGS. 9A-9D are schematic diagrams of example implementations of objective bypass illuminators that may be used with the fluorescent microscopy system in FIG. 8.

In an example implementation, an objective bypass is provided to guide the excitation light around the objective lens 830. FIGS. 9A-9D are schematic diagrams of example implementations of objective bypass illuminators that may be used with the fluorescent microscopy system in FIG. 8. Referring to FIG. 9A, a first objective lens bypass system 900 includes a beam shaping element 902, and a redirecting element 904. The excitation light 828 (shown in FIG. 8) may be directed to the beam shaping element 902, which may be implemented using an achromatic lens that focuses substantially collimated light. The beam shaping element 902 directs the excitation light to the redirecting element 904, which may be a first surface mirror. The redirecting element 904 directs the excitation light to focus on a sample 910 as shown at 906. The sample 910 fluoresces an emission light 912 into the objective lens 920. The objective lens 918 directs the emission light 912 to the detector 840 (in FIG. 8).

The objective bypass 900 in FIG. 9A removes the excitation light from the optical path in the objective lens 918. The objective bypass 900 may be connected to the objective lens 912 so that the beam shaping element 902 and the redirecting element 904 may move together with the objective lens 912 during focusing operations. It is noted that the beam shaping element 902 may be implemented by other lenses such as Fresnel lenses or molded aspheres.

Figure 9B:
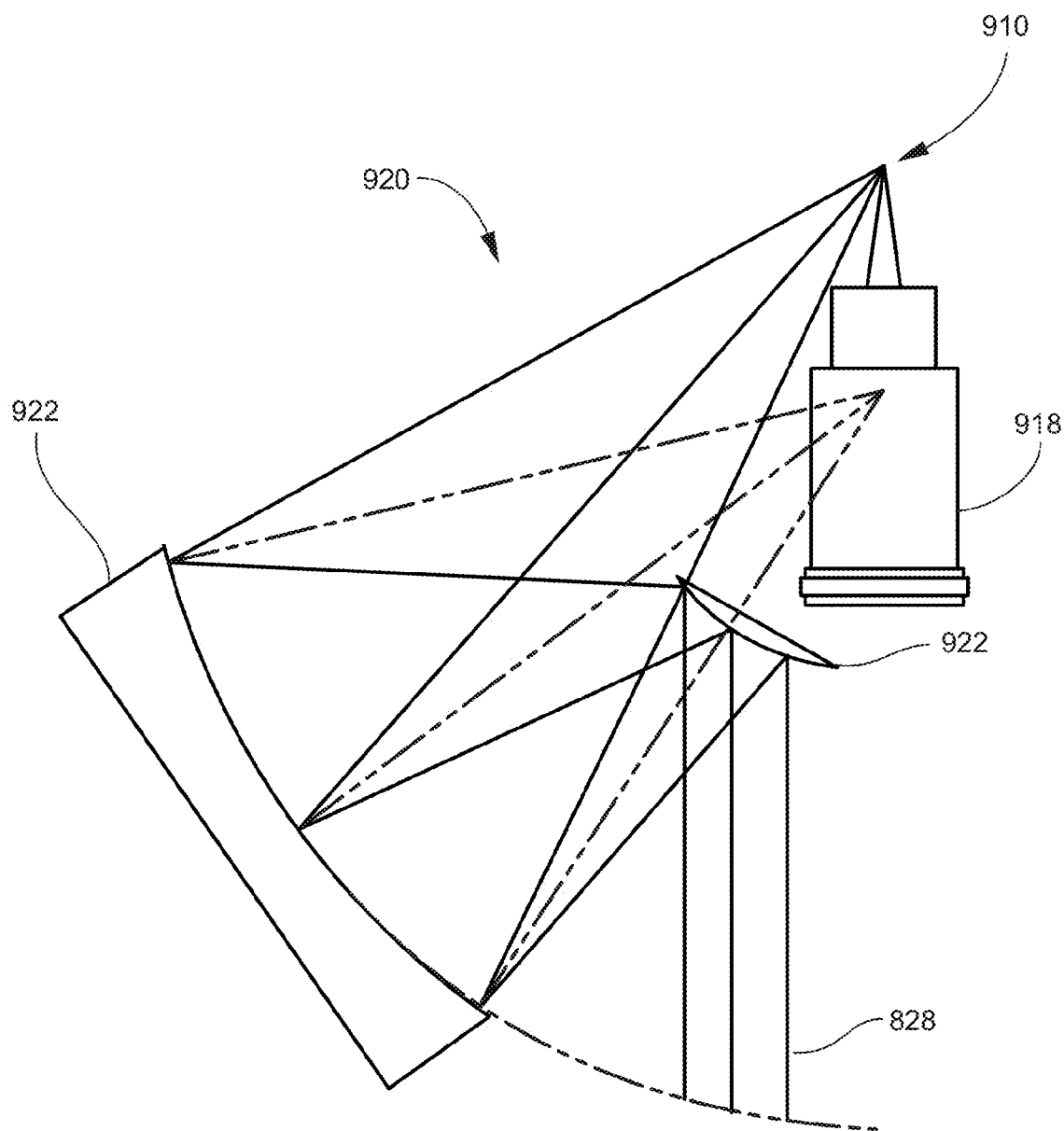

FIG. 9B shows an alternative implementation of an objective bypass 920 in which the excitation light 828 bypasses the objective 918 using two powered mirrors: a convex, spherical mirror 922 and a concave spherical mirror 924. The convex, spherical mirror 922 receives the excitation light 828 and directs it to the concave spherical mirror 924. The concave spherical mirror 924 directs the excitation light to the sample 910. The objective 918 is depicted as having a narrower body, which may be compared with having the outer cover removed. A narrower objective 918 body may increase oblique illumination access to the sample 910.

Figure 9C:
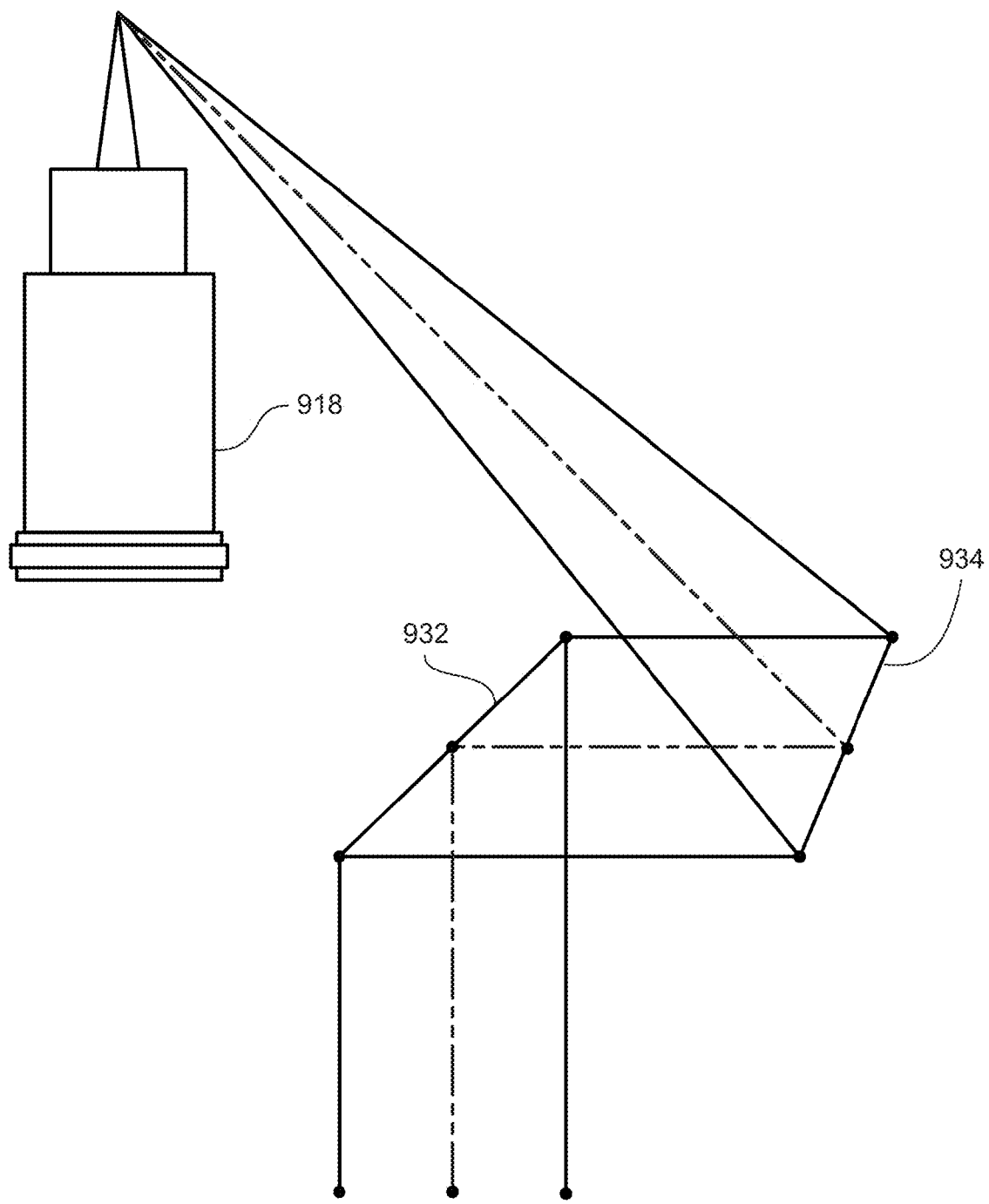

FIG. 9C shows an alternate implementation of an objective bypass 930 implemented using a flat mirror 932 to receive the excitation light, and an off-axis parabolic mirror 934 to receive the excitation light reflected off the flat mirror 932 and to redirect the excitation light towards the sample 910.

Figure 9D:
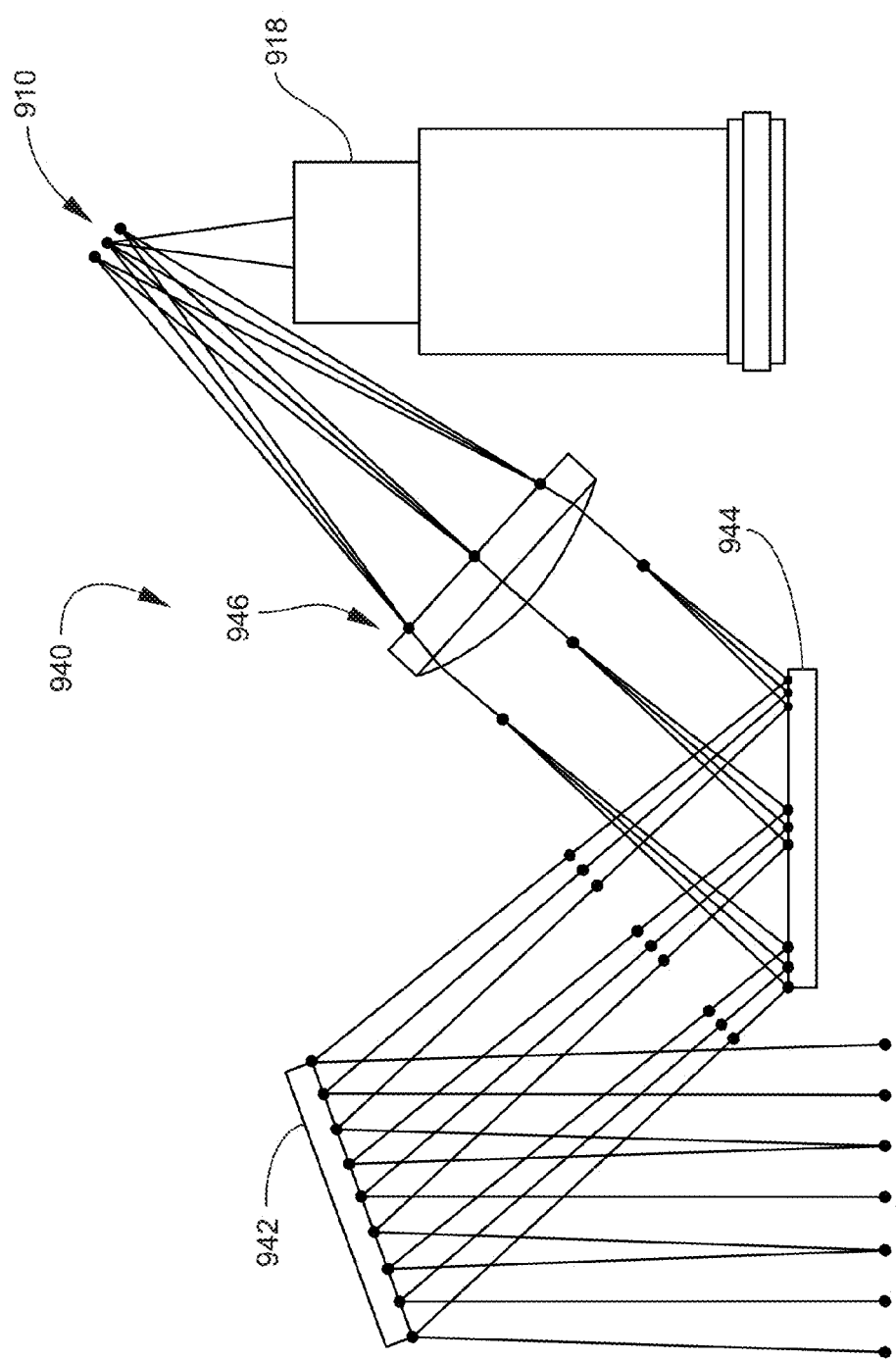

FIG. 9D shows an alternative embodiment of an objective bypass 940 implemented using a flat mirror 942 to receive the excitation light. The flat mirror 942 reflects the excitation light to second flat mirror 944, which reflects the excitation light to an aspheric singlet 946, which may be molded from acrylic.

It is noted that the objective bypass 910, 920, 930, and 940 may or may not be configured to move with the objective 918 when focusing. In some implementations, the focusing element of the objective bypass may be fixed relative to the objective 918, and the redirecting element may move with the objective 918. In other implementations, both the focusing element and the redirecting element may be fixed relative to the moving objective 918.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A system for analyzing a target in a sample, the target being capable of generating an emitted light, the system comprising:
   an excitation light source configured to generate an excitation light along an excitation optical path;
   a plurality of detectors each configured to measure an optical characteristic in an emission light, the plurality of detectors including at least one monochromator-based measurement detector;
   an excitation monochromator configured to receive the excitation light and to output a selected wavelength component of the excitation light along the excitation optical path when the target in the sample generates the emitted light in response to the excitation light;
   a sample carrier configured to position the sample to receive the excitation light and to generate the emitted light along one of a plurality of selectable emission optical paths;
   a cartridge carrier configured to support a plurality of removable cartridges having a common form factor, the cartridges including application cartridges that support filter-based measurements, and to move the removable cartridges to a selected position;
   an emission monochromator configured to receive the emitted light from the sample along a main measurement optical axis, and to output a selected wavelength component of the emitted light along the selected emission optical path when the selected one of the plurality of selectable emission optical paths includes the emission monochromator;

an interface cartridge having the common form factor for removably mounting on the cartridge carrier, the interface cartridge comprising a plurality of emission light ports each positioned to direct the emitted light from the sample along a corresponding one of a plurality of optical paths, where the interface cartridge is positioned to align a selected one of the plurality of optical paths with the main measurement optical axis;

a movable sliding switch mechanism comprising a plurality of optical channels each corresponding to a position on the sliding switch mechanism and each optical channel configured to complete a corresponding one of the plurality of selectable emission optical paths, where the position on the sliding switch mechanism is selected by moving the sliding switch mechanism to align the optical channel for the position with the main measurement optical axis;

a bottom plate in a housing for mounting the interface cartridge, the sliding switch mechanism, the excitation monochromator, the emission monochromator, and the cartridge carrier;

a chamber disposed under bottom plate; where the chamber includes a first opening above the sample carrier and a second opening below the sample carrier aligned with the first opening;

a fluorescence bottom measurement head positioned under the chamber and aligned with the second opening of the chamber, the fluorescence bottom measurement head including an excitation fiber head port, an emission fiber head port, and connection optics to guide the excitation light received at the excitation fiber head port to the sample and the emitted light received from the sample to the emission fiber head port to obtain measurements of the sample from below the sample;

where the plurality of optical paths in the interface cartridge includes a bottom measurement path configured to direct the excitation light to an excitation fiber connected to the excitation fiber head port; and the optical channel in one of the positions of the sliding switch mechanism is optically connected to an emission fiber connected to the emission fiber head port.

2. The system of claim 1, further comprising:
an x-y transport for supporting the sample carrier, the x-y transport positioned in the chamber.

3. The system of claim 2, where
the plurality of detectors includes a photodiode for absorbance measurements mounted on an absorbance read head positioned under the chamber with the photodiode aligned with the second opening of the chamber; and
one of the plurality of optical paths in the interface cartridge includes an absorbance light path for directing the excitation light to the sample via the first opening.

4. The system of claim 2, further comprising:
an imaging system interface configured to enable an optical light path from an imaging system to align optically with the sample on the sample carrier at the first and second openings to enable imaging of the sample.

5. The system of claim 4, further comprising:
an imaging system application cartridge removably mounted on the cartridge carrier, where the cartridge carrier is configured to position the imaging system application cartridge to enable functions to supplement operation of the imaging system.

6. The system of claim 5, where the imaging system application cartridge includes an illumination cartridge comprising a light source, the illumination cartridge configured to illuminate the imaging system via the imaging system interface.

7. The system of claim 5, where the imaging system application cartridge includes an injector cartridge comprising selected fluid reagents and an injector nozzle, the injector cartridge configured to position the injector nozzle over the sample and to inject selected fluid reagents in the sample.

8. The system of claim 5, where the imaging system application cartridge includes an epifluorescence-based imaging application cartridge.

9. The system of claim 1, where the plurality of optical paths in the interface cartridge include:
a top fluorescence measurement path comprising fluorescence connection optics at a top fluorescence measurement port and optical guides for directing the emitted light to the main measurement path;
a top luminescence measurement path comprising luminescence connection optics at a top luminescence measurement port and optical guides for directing the emitted light to the main measurement path;
where the interface cartridge is moved to select the top fluorescence measurement path for fluorescence measurements from above the sample or to select the top luminescence measurement path for luminescence measurements.

10. The system of claim 1, where the plurality of detectors includes at least one photomultiplier tube ("PMT"); and
the positions of the sliding switch mechanism includes:
a first position where the first position optical channel aligns the main measurement path with the emission monochromator; and
a second position where the second position optical channel directs the emitted light received along the main measurement path to the at least one PMT.

11. The system of claim 10, where the at least one PMT is a first PMT, and the plurality of detectors includes a second PMT; the second position optical channel directs the emitted light to the first PMT: and the positions of the sliding switch mechanism includes:
a third position where the third position optical channel directs the emitted light received along the main measurement path to the second PMT.

12. The system of claim 11, where the cartridge carrier is configured to selectably move the interface cartridge away from the main measurement optical axis, and to position an application cartridge having a first emission light output level with the main measurement optical axis and a selectable second emission light output at a lower level than the first emission light output to align the first emission light output with the main measurement optical axis.

13. A monchromator-based system for analyzing a target in a sample, the target being capable of generating an emitted light, comprising:
an excitation light source configured to generate an excitation light along an excitation optical path;
a plurality of detectors each configured to measure an optical characteristic in an emission light, the plurality of detectors including at least one monochromator-based measurement detector:
an excitation monochromator configured to receive the excitation light and to output a selected wavelength component of the excitation light along the excitation optical path when the target in the sample generates the emitted light in response to the excitation light;

a sample carrier configured to position the sample to receive the excitation light and to generate the emitted light along one of a plurality of selectable emission optical paths;

a cartridge carrier configured to support a plurality of removable cartridges having a common form factor, the cartridges including application cartridges that support filter-based measurements, and to move the removable cartridges to a selected position;

an emission monochromator configured to receive the emitted light from the sample along a main measurement optical axis, and to output a selected wavelength component of the emitted light along the selected emission optical path when the selected one of the plurality of selectable emission optical paths includes the emission monochromator;

an interface cartridge having the common form factor for removably mounting on the cartridge carrier, the interface cartridge comprising a plurality of emission light ports each positioned to direct the emitted light from the sample along a corresponding one of a plurality of optical paths, where the interface cartridge is positioned to align a selected one of the plurality of optical paths with the main measurement optical axis;

a movable sliding switch mechanism comprising a plurality of optical channels each corresponding to a position on the sliding switch mechanism and each optical channel configured to complete a corresponding one of the plurality of selectable emission optical paths, where the position on the sliding switch mechanism is selected by moving the sliding switch mechanism to align the optical channel for the position with the main measurement optical axis; wherein the excitation monochromator and the emission monochromator are configured as dual-monochromators each having first and second angularly movable gratings, the monochromators mounted in the system to receive corresponding light paths in parallel, the system further comprising:

an optics configuration panel positioned between the dual-monochromators and the sliding switch mechanism, the optics configuration panel comprising:

an excitation monochromator entrance slit aligned with the first grating of the excitation monochromator and with the excitation optical path;

an excitation monochromator exit slit aligned with a selected wavelength component of the excitation light when the second grating of the excitation monochromator is rotated to align the selected wavelength component with the excitation monochromator slit;

an emission monochromator entrance slit aligned with the first grating of the emission monochromator and with the main measurement optical path; and an emission monochromator exit slit aligned with a selected wavelength component of the emitted light from the sample when the second grating of the emission monochromator is rotated to align the selected wavelength component with the emission monochromator slit.

14. The system of claim 13, where the optics configuration panel further comprises:
at least one switch configured to switch a selected one of a plurality of optical components to condition either the excitation light or the emission light.

15. The system of claim 14, where the plurality of optical components includes any of:
a filter to adjust a bandwidth of either the excitation light or the emission light;
a polarizing filter;
an order-sorting filter;
a slit adjusted to a wavelength dispersion of the 2nd order to enable using a grating in 2nd order for deep UV absorbance measurements;
an attenuation filter.

16. A fluorescent microscopy system comprising:
a fluorescent dye excitation apparatus comprising a light source to output a light, and an optical system configured to convert the light into an excitation beam having a distribution of light flux suitable for simultaneously lighting substantially all of the field of view the microscope;
a detector configured to detect an imaging light from a specimen;
an objective lens adjustably positioned to receive imaging light from the specimen and to focus the imaging light along a path to the detector; and
an objective bypass disposed in the excitation beam path to receive the excitation beam, to focus the excitation beam, and to direct the excitation beam to focus on a sample plane of the specimen,
wherein the objective bypass comprises at least one mirror and is provided to guide the excitation light around the objective lens, and
wherein the objective bypass and the objective lens are connected to enable the objective bypass to move in concert with the objective lens during focusing functions.

17. The fluorescent microscopy system of claim 16, where the objective bypass comprises:
a beam-shaping element disposed in the excitation beam path to receive the excitation beam and to focus substantially collimated light to a sample plane of the specimen, and
a redirecting element to direct the substantially collimated light to focus on the specimen.

18. The fluorescent microscopy system of claim 17, where the redirecting element includes a first flat mirror configured to receive the excitation beam and to reflect the excitation beam at an angle to second flat mirror configured to receive the reflected excitation beam and to reflect the reflected excitation beam at an angle towards the sample; and the beam-shaping element in the objective bypass is a molded acrylic asphere positioned to focus the excitation beam received from the second mirror on the specimen.

19. The fluorescent microscopy system of claim 18, where the combination of mirrors includes a convex spherical mirror positioned to reflect the excitation beam to a concave spherical mirror positioned to focus the excitation beam on the sample.

20. The fluorescent microscopy system of claim 16, where the beam-shaping element in the objective bypass is one of an achromatic lens, a Fresnel lens, or a molded asphere.

21. The fluorescent microscopy system of claim 16, where the objective bypass comprises a combination of powered mirrors.

* * * * *